(12) United States Patent
Hernandez-Rosas et al.

(10) Patent No.: US 9,974,469 B2
(45) Date of Patent: May 22, 2018

(54) SYSTEMS AND METHODS FOR A CONTINUOUS MONITORING OF ANALYTE VALUES

(71) Applicant: DexCom, Inc., San Diego, CA (US)

(72) Inventors: Jose Hector Hernandez-Rosas, San Diego, CA (US); Shawn Larvenz, Ramona, CA (US); Mark Dervaes, Carlsbad, CA (US); Indrawati Gauba, San Diego, CA (US); Michael Robert Mensinger, San Diego, CA (US); Eric Cohen, San Diego, CA (US); Brian Christopher Smith, San Marcos, CA (US); Jorge Valdes, San Diego, CA (US); Jacob S. Leach, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 185 days.

(21) Appl. No.: 14/533,943

(22) Filed: Nov. 5, 2014

(65) Prior Publication Data

US 2015/0123810 A1   May 7, 2015

Related U.S. Application Data

(60) Provisional application No. 61/901,358, filed on Nov. 7, 2013.

(51) Int. Cl.
*G08B 23/00*  (2006.01)
*G08C 15/06*  (2006.01)
(Continued)

(52) U.S. Cl.
CPC ........ *A61B 5/14503* (2013.01); *A61B 5/0004* (2013.01); *A61B 5/076* (2013.01);
(Continued)

(58) Field of Classification Search
CPC . G06F 19/3418; G06F 19/3406; H04L 63/04; H04L 63/08; H04W 12/06;
(Continued)

(56) References Cited

U.S. PATENT DOCUMENTS 6,148,051 A   11/2000   Fujimori et al.
6,175,752 B1   1/2001   Say et al.
(Continued)

FOREIGN PATENT DOCUMENTS

CA   2690742 A1   12/2008
EP   1445893 A2   8/2004
(Continued)

OTHER PUBLICATIONS

Wikipedia 2013. "Background Process", retrieved from Internet on Jan. 20, 2015 from http://wikipedia.org/w/index.php?title=Background_process&oldid=560905854. [4 pages].
(Continued)

*Primary Examiner* — Firmin Backer
*Assistant Examiner* — Jerold Murphy
(74) *Attorney, Agent, or Firm* — Knobbe Martens Olson & Bear, LLP

(57) ABSTRACT

Systems and methods for a continuous monitoring of analyte values received from an analyte sensor system are provided. One method for a wireless data communication between an analyte sensor system and a mobile device involves storing identification information associated with a transceiver of the analyte sensor system, the identification information entered by a user of the mobile device via a custom application running on the mobile device; causing the custom application to enter a background mode; searching for advertisement signals; receiving an advertisement signal from the transceiver; authenticating the transceiver based on the identification information; prompting the user to bring
(Continued)

the custom application to a foreground mode; causing the custom application to request a confirmation from the user that a data connection with the transceiver is desired; receiving the confirmation from the user; and completing the data connection with the transceiver.

18 Claims, 13 Drawing Sheets

(51) Int. Cl.
　　*G08C 19/22*　　(2006.01)
　　*H04Q 9/00*　　(2006.01)
　　*A61B 5/00*　　(2006.01)
　　*A61B 5/145*　　(2006.01)
　　*H04Q 9/14*　　(2006.01)
　　*H04B 7/26*　　(2006.01)
　　*H04L 29/08*　　(2006.01)
　　*A61B 5/07*　　(2006.01)

(52) U.S. Cl.
　　CPC .......... *A61B 5/14532* (2013.01); *A61B 5/742* (2013.01); *H04B 7/26* (2013.01); *H04L 67/12* (2013.01); *H04Q 9/00* (2013.01); *H04Q 9/14* (2013.01); *H04W 4/70* (2018.02); *H04W 76/10* (2018.02); *H04W 76/14* (2018.02); *H04W 76/30* (2018.02); *H04W 76/34* (2018.02); *H04Q 2209/40* (2013.01); *H04Q 2209/50* (2013.01)

(58) Field of Classification Search
　　CPC ................. H04W 4/005; H04W 4/008; A61M 2205/3576; A61M 2205/3592; A61M 5/1723; H04J 3/0667; A61B 5/14532; A61B 5/0002; A61B 5/0022; A61B 5/01; A61B 5/0015
　　See application file for complete search history.

(56) References Cited

U.S. PATENT DOCUMENTS

| | | | |
|---|---|---|---|
| 6,219,669 B1 * | 4/2001 | Haff | .................. H04L 29/06 |
| 6,535,980 B1 | 3/2003 | Kumar | |
| 6,564,105 B2 | 5/2003 | Starkweather et al. | |
| 6,571,128 B2 | 5/2003 | Lebel et al. | |
| 6,585,644 B2 | 7/2003 | Lebel et al. | |
| 6,659,948 B2 | 12/2003 | Lebel et al. | |
| 6,811,533 B2 | 11/2004 | Lebel et al. | |
| 6,811,534 B2 | 11/2004 | Bowman et al. | |
| 6,813,519 B2 | 11/2004 | Lebel et al. | |
| 6,958,705 B2 | 10/2005 | Lebel et al. | |
| 7,098,803 B2 | 8/2006 | Mann et al. | |
| 7,120,750 B1 | 10/2006 | Seidl et al. | |
| 7,369,634 B2 | 5/2008 | Spital et al. | |
| 7,369,635 B2 | 5/2008 | Spital et al. | |
| 7,519,408 B2 | 4/2009 | Rasdal et al. | |
| 7,587,287 B2 | 9/2009 | Connolly et al. | |
| 7,630,407 B2 | 12/2009 | Compton et al. | |
| 7,722,536 B2 | 5/2010 | Goodnow | |
| 7,768,408 B2 | 8/2010 | Reggiardo et al. | |
| 7,801,582 B2 | 9/2010 | Peyser | |
| 7,811,231 B2 | 10/2010 | Jin et al. | |
| 7,826,382 B2 | 11/2010 | Sicurello et al. | |
| 7,884,729 B2 | 2/2011 | Reggiardo et al. | |
| 7,948,370 B2 | 5/2011 | Reggiardo et al. | |
| 7,949,404 B2 | 5/2011 | Hill | |
| 8,029,443 B2 | 10/2011 | Goodnow | |
| 8,066,639 B2 | 11/2011 | Nelson et al. | |
| 8,085,151 B2 | 12/2011 | Jennewine | |
| 8,086,292 B2 | 12/2011 | Peyser | |
| 8,089,363 B2 | 1/2012 | Reggiardo et al. | |
| 8,123,686 B2 | 2/2012 | Fennell et al. | |
| 8,187,183 B2 | 5/2012 | Jin et al. | |
| 8,226,556 B2 | 7/2012 | Hayes et al. | |
| 8,233,456 B1 | 7/2012 | Kopikare et al. | |
| 8,372,351 B2 | 2/2013 | Ow-Wing | |
| 8,407,759 B1 * | 3/2013 | Sotos | ..................... H04L 69/14 |
| | | | 370/328 |
| 8,437,966 B2 | 5/2013 | Connolley et al. | |
| 8,644,823 B2 | 2/2014 | Rozinov | |
| 8,844,007 B2 | 9/2014 | Vicente et al. | |
| 8,935,352 B1 | 1/2015 | Perrella et al. | |
| 9,092,427 B2 | 7/2015 | Mackler | |
| 9,094,379 B1 | 7/2015 | Miller | |
| 9,098,114 B2 | 8/2015 | Potter et al. | |
| 9,386,522 B2 | 7/2016 | San Vicente et al. | |
| 9,398,399 B2 | 7/2016 | Preiszler et al. | |
| 9,445,445 B2 | 9/2016 | Miller et al. | |
| 2002/0046300 A1 | 4/2002 | Hanko et al. | |
| 2004/0152958 A1 | 8/2004 | Frei et al. | |
| 2005/0096009 A1 | 5/2005 | Ackley | |
| 2005/0182306 A1 | 8/2005 | Sloan | |
| 2006/0001538 A1 | 1/2006 | Kraft | |
| 2006/0166629 A1 | 7/2006 | Reggiardo | |
| 2006/0173259 A1 | 8/2006 | Flaherty et al. | |
| 2007/0100222 A1 | 5/2007 | Mastrototaro et al. | |
| 2007/0207750 A1 | 9/2007 | Brown | |
| 2007/0253021 A1 | 11/2007 | Mehta et al. | |
| 2007/0258395 A1 | 11/2007 | Jollota et al. | |
| 2008/0031208 A1 | 2/2008 | Abishek et al. | |
| 2008/0060955 A1 | 3/2008 | Goodnow | |
| 2008/0092638 A1 | 4/2008 | Brenneman et al. | |
| 2008/0278332 A1 | 11/2008 | Fennell | |
| 2008/0294020 A1 | 11/2008 | Sapounas | |
| 2005/0320587 A1 | 12/2008 | Vauclair et al. | |
| 2008/0300572 A1 | 12/2008 | Rankers et al. | |
| 2008/0301436 A1 | 12/2008 | Yao et al. | |
| 2008/0312518 A1 | 12/2008 | Jina et al. | |
| 2008/0319296 A1 | 12/2008 | Bernstein et al. | |
| 2008/0320587 A1 | 12/2008 | Vauclair et al. | |
| 2009/0028006 A1 | 1/2009 | Ha et al. | |
| 2009/0117844 A1 | 1/2009 | Li et al. | |
| 2009/0036760 A1 | 2/2009 | Hayter | |
| 2009/0076358 A1 | 3/2009 | Reggiardo et al. | |
| 2009/0076359 A1 | 3/2009 | Peyser | |
| 2009/0085768 A1 | 4/2009 | Patel et al. | |
| 2009/0094680 A1 | 4/2009 | Gupta et al. | |
| 2009/0105571 A1 | 4/2009 | Fennell et al. | |
| 2009/0119190 A1 | 5/2009 | Realini et al. | |
| 2009/0203982 A1 | 8/2009 | Nelson et al. | |
| 2009/0216102 A1 | 8/2009 | Say et al. | |
| 2009/0022126 A1 | 9/2009 | Soliman et al. | |
| 2009/0221261 A1 | 9/2009 | Soliman et al. | |
| 2009/0237216 A1 | 9/2009 | Twitchell, Jr. | |
| 2009/0240120 A1 | 9/2009 | Mensinger et al. | |
| 2009/0240193 A1 | 9/2009 | Mensinger et al. | |
| 2009/0257354 A1 | 10/2009 | Hannel et al. | |
| 2009/0284372 A1 | 11/2009 | Nelson et al. | |
| 2009/0296742 A1 | 12/2009 | Sicurello et al. | |
| 2009/0300616 A1 | 12/2009 | Sicurello et al. | |
| 2010/0074383 A1 | 3/2010 | Lee et al. | |
| 2010/0076280 A1 | 3/2010 | Bernstein et al. | |
| 2010/0076288 A1 | 3/2010 | Connolly et al. | |
| 2010/0076289 A1 | 3/2010 | Bernstein et al. | |
| 2010/0076290 A1 | 3/2010 | Bernstein et al. | |
| 2010/0076291 A1 | 3/2010 | Bernstein et al. | |
| 2010/0076292 A1 | 3/2010 | Bernstein et al. | |
| 2010/0076293 A1 | 3/2010 | Bernstein et al. | |
| 2010/0082266 A1 | 4/2010 | Connolly et al. | |
| 2010/0082364 A1 | 4/2010 | Taub et al. | |
| 2010/0094111 A1 | 4/2010 | Heller et al. | |
| 2010/0110931 A1 | 5/2010 | Shim et al. | |
| 2010/0217660 A1 | 8/2010 | Biswas et al. | |
| 2010/0250230 A1 | 9/2010 | Ganguly et al. | |
| 2010/0265073 A1 | 10/2010 | Harper | |
| 2010/0275108 A1 | 10/2010 | Sloan et al. | |
| 2010/0277342 A1 | 11/2010 | Sicurello et al. | |
| 2010/0309001 A1 | 12/2010 | Connolly et al. | |
| 2011/0003610 A1 | 1/2011 | Key et al. | |
| 2011/0004085 A1 | 1/2011 | Mensinger et al. | |
| 2011/0009272 A1 | 1/2011 | Mensinger et al. | |

(56) References Cited

U.S. PATENT DOCUMENTS

| | | |
|---|---|---|
| 2011/0009727 A1 | 1/2011 | Mensinger et al. |
| 2011/0015502 A1 | 1/2011 | Peyser |
| 2011/0015508 A1 | 1/2011 | Peyser |
| 2011/0015509 A1 | 1/2011 | Peyser |
| 2011/0035582 A1 | 2/2011 | Zheng |
| 2011/0044333 A1 | 2/2011 | Sicurello et al. |
| 2011/0046469 A1 | 2/2011 | Nelson et al. |
| 2011/0058485 A1 | 3/2011 | Sloan |
| 2011/0081888 A1 | 4/2011 | Waniss |
| 2011/0144806 A1* | 6/2011 | Sandhu .............. A61B 19/2203 700/264 |
| 2011/0184265 A1 | 7/2011 | Hayter |
| 2011/0213225 A1 | 9/2011 | Bernstein et al. |
| 2014/0213225 A1 | 9/2011 | Bernstein et al. |
| 2011/0289497 A1 | 11/2011 | Kiaie et al. |
| 2011/0320130 A1 | 12/2011 | Valdes et al. |
| 2012/0010857 A1 | 1/2012 | Richeter et al. |
| 2012/0053428 A1 | 3/2012 | Bernstein et al. |
| 2012/0078071 A1* | 3/2012 | Bohm .................. G06F 1/3203 600/345 |
| 2012/0092168 A1 | 4/2012 | Jennewine |
| 2012/0101352 A1 | 4/2012 | Peyser |
| 2012/0101353 A1 | 4/2012 | Reggiardo et al. |
| 2012/0158907 A1 | 6/2012 | Fennell et al. |
| 2012/0229299 A1 | 9/2012 | Skoldengen et al. |
| 2012/0232368 A1 | 9/2012 | Jin et al. |
| 2012/0245447 A1 | 9/2012 | Karan et al. |
| 2012/0260323 A1* | 10/2012 | San Vicente ........... A61B 5/002 726/6 |
| 2012/0274443 A1* | 11/2012 | Kai ...................... A61B 5/0002 340/5.61 |
| 2013/0035575 A1 | 2/2013 | Mayou et al. |
| 2013/0059541 A1 | 3/2013 | Sloan et al. |
| 2013/0078912 A1 | 3/2013 | San Vicente et al. |
| 2013/0232550 A1 | 9/2013 | Kihara et al. |
| 2014/0040984 A1 | 2/2014 | Mackler et al. |
| 2014/0206972 A1 | 7/2014 | Hayter et al. |
| 2014/0218496 A1 | 8/2014 | Park et al. |
| 2014/0273821 A1 | 9/2014 | Miller et al. |
| 2015/0123811 A1 | 5/2015 | Hernandez-Rosas et al. |

FOREIGN PATENT DOCUMENTS

| | | |
|---|---|---|
| EP | 2172863 A2 | 4/2010 |
| WO | WO 2006-079114 | 7/2006 |
| WO | WO 2008-106645 | 9/2008 |
| WO | WO 2009-018058 | 2/2009 |
| WO | WO 2009-051832 | 4/2009 |
| WO | WO 2009-105709 | 8/2009 |
| WO | WO 2009-146390 | 12/2009 |
| WO | WO 2009-146391 | 12/2009 |
| WO | WO 2010-039746 | 4/2010 |
| WO | WO 2010/039746 | 4/2010 |
| WO | WO 2012-010353 | 4/2012 |
| WO | WO 2012-108935 | 8/2012 |
| WO | WO 2012/108985 | 8/2012 |

OTHER PUBLICATIONS

Wikipedia 2013. "Graphical User Interface", retrieved from internet on Jan. 20, 2015 from http://en.wikipedia.org/w/index.php?title=Graphical_User_Interrace&oldid=579694866.

Dynastream Innovations, Inc.: ANT Message Protocol and Usage (Jul. 2, 2007).

Texas Instruments Incorporated: 1- and 8-Channel ANT RF Network Processors (2011).

IEEE Std 802. 11-2007—Revision of IEEE Std 801. 11-1999), Jun. 12, 2007, Institute of Electrical and Engineers, Inc., pp. 1, 3, 61, 79, 468, 591-594.

Lai et al. 2003. IEEE 802.11 Ad-hoc-mode timing synchronization function, 176h Intl Conf on Advanced Information Networking & Applications (AINA 2003), Mar. 29, 2003, Xian, CHIN.

* cited by examiner

SYSTEMS AND METHODS FOR A CONTINUOUS MONITORING OF ANALYTE VALUES

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 61/901,358 filed Nov. 7, 2013. The aforementioned application is incorporated by reference herein in its entirety, and is hereby expressly made a part of this specification.

FIELD

Systems and methods for a continuous monitoring of analyte values received from an analyte sensor system are provided.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is going up (higher) or down (lower) based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

In a first aspect, a method for a wireless data communication between an analyte sensor system and a mobile device capable of wirelessly receiving analyte values from the analyte sensor system is provided. The method can comprise storing identification information associated with a transceiver of the analyte sensor system, the identification information entered by a user of the mobile device via a custom application running on the mobile device; causing the custom application to enter a background mode; searching for advertisement signals; receiving an advertisement signal from the transceiver; authenticating the transceiver based on the identification information; prompting the user to bring the custom application to a foreground mode; causing the custom application to request a confirmation from the user that a data connection with the transceiver is desired; receiving the confirmation from the user; and completing the data connection with the transceiver.

In certain implementations of the first aspect, which is generally applicable, particularly with any other implementation of the first aspect, the method can further comprise receiving an analyte value from the transceiver; terminating the data connection with the transceiver; entering an inactive mode; exiting the inactive mode after a predetermined time; and searching for advertisement signal from the transceiver.

In certain implementations of the first aspect, which is generally applicable, particularly with any other implementation of the first aspect, the authenticating step can comprise requesting a challenge value from the transceiver; receiving the challenge value from the transceiver; generating a hash value from the challenge value and the identification information; transmitting the hash value to the transceiver; and receiving a confirmation indicating a successful authentication from the transceiver.

In certain implementations of the first aspect, which is generally applicable, particularly with any other implementation of the first aspect, the method can further comprise determining that an excessive memory is being used by the custom application; causing the custom application to enter a suspended state; determining a next scheduled time at which the custom application is expected to search for advertisement signals from the transceiver; and causing the custom application to exit the suspended state prior to the next scheduled time.

In a second aspect is provided a mobile device configured for a wireless data communication with an analyte sensor system, comprising: a user interface; a radio unit for transmitting and receiving wireless signals; a memory for storing identification information associated with one or more transceivers and a custom application configured to interact with a user of the mobile device via the user interface; and a processor operatively coupled to the user interface, the radio unit, and the memory and configured to: cause the custom application to enter a background mode, cause the radio unit to search for advertisement signals, perform an authentication procedure with a transceiver of the analyte sensor system based on user-entered identification information associated with the transceiver if an advertisement signal is received from the transceiver, issue a first notification to the user to bring the custom application into a foreground mode, cause the custom application to issue a second notification requesting the user for a confirmation that a data connection with the transceiver is desired, and complete the data connection with the transceiver if the confirmation is received.

In certain implementations of the second aspect, which is generally applicable, particularly with any other implementation of the second aspect, the analyte sensor system can be a continuous glucose sensor system.

In certain implementations of the second aspect, which is generally applicable, particularly with any other implementation of the second aspect, the user interface can comprise a voice user interface.

In certain implementations of the second aspect, which is generally applicable, particularly with any other implementation of the second aspect, the user interface can comprise a touch screen display.

In certain implementations of the second aspect, which is generally applicable, particularly with any other implementation of the second aspect, the first notification can be a pop-up menu displayed on the touch screen display.

In certain implementations of the second aspect, which is generally applicable, particularly with any other implementation of the second aspect, the wireless data communication can employ a communication protocol designed for a short distance and low-power wireless communication.

In certain implementations of the second aspect, which is generally applicable, particularly with any other implementation of the second aspect, the processor can be further configured to determine that an excessive memory space has been used by the custom application; cause the custom application to enter a suspended state, cause the custom application to exit the suspended state prior to a scheduled time at which the mobile device is expected to search for a next advertisement signal from the transceiver, and cause the custom application to search for the next advertisement signal in a background mode.

In certain implementations of the second aspect, which is generally applicable, particularly with any other implementation of the second aspect, the processor can be further configured to determine that an excessive memory is being used by the custom application; cause the custom application to enter a suspended state, determine a next scheduled time at which the transceiver is expected to begin transmitting a series of advertisement signals, cause the custom application to exit the suspended state prior to the next scheduled time, and cause the radio unit to search for the advertisement signals.

In certain implementations of the second aspect, which is generally applicable, particularly with any other implementation of the second aspect, the processor can be further configured to determine that an excessive memory is being used by the custom application, cause the custom application to enter a suspended state, determine a next scheduled time at which the transceiver is expected to begin transmitting a series of advertisement signals, and cause the radio to search for the advertisement signals at the next scheduled time while the custom application is still in the suspended state.

In a third aspect is provided a method for a wireless data communication between an analyte sensor system and a mobile device capable of wirelessly receiving analyte values from the analyte sensor system, the method comprising: transmitting a first series of advertisement signals beginning at a first time; receiving a data connection request from a mobile device at a second time; establishing a data connection with the mobile device; transmitting a connection interval indicative of a difference between the second time and the first time to the mobile device; transmitting an analyte value; terminating the data connection with the mobile device; and causing a transceiver of the analyte sensor system to enter a sleep state.

In certain implementations of the third aspect, which is generally applicable, particularly with any other implementation of the third aspect, the method can further comprise causing the transceiver to exit the sleep mode after a predetermined time; and transmitting a second series of advertisement signals.

In certain implementations of the third aspect, which is generally applicable, particularly with any other implementation of the third aspect, the predetermine time can be between about 200 and 400 seconds.

In certain implementations of the third aspect, which is generally applicable, particularly with any other implementation of the third aspect, the analyte value can be based on an analyte measurement taken while the transceiver was in a previous sleep mode.

In a fourth aspect is provided a method for a wireless data communication between an analyte sensor system and a mobile device capable of wirelessly receiving analyte values from the analyte sensor system, the method comprising: searching for advertisement signals; receiving an advertisement signal from a transceiver of the analyte sensor system; transmitting a data connection request to the transceiver; establishing a data connection with the transceiver if the data connection request is granted; receiving a connection interval indicative of a difference between a first time at which the transceiver started to transmit a series of advertisement signals and a second time at which the transceiver received the data connection request from the mobile device; receiving an analyte value from the transceiver; terminating the data connection with the transceiver, thereby causing the transceiver to enter a sleep mode; entering an inactive mode during which the mobile device does not communicate with the transceiver; calculating an exit time at which the mobile device is to exit the inactive mode based at least partly on the connection interval; exiting the inactive mode at the exit time; and search for advertisement signals after exiting the inactive mode.

In certain implementations of the fourth aspect, which is generally applicable, particularly with any other implementation of the fourth aspect, the analyte value can be based on an analyte measurement taken while the transceiver was in a previous sleep mode.

In certain implementations of the fourth aspect, which is generally applicable, particularly with any other implementation of the fourth aspect, the exit time can be given by current time+update interval−the connection interval−notification delay−safeguard, the update interval can be a time duration between two consecutive wireless communication sessions between the transceiver and the mobile device.

In certain implementations of the fourth aspect, which is generally applicable, particularly with any other implementation of the fourth aspect, the update interval can be between about 200 and 400 seconds.

In certain implementations of the fourth aspect, which is generally applicable, particularly with any other implementation of the fourth aspect, the connection interval can be between about 90 and 300 milliseconds.

In certain implementations of the fourth aspect, which is generally applicable, particularly with any other implementation of the fourth aspect, the notification delay can be between about 100 and 300 milliseconds and the safeguard is typically between about 300 and 700 milliseconds.

In a fifth aspect is provided an analyte sensor system configured for a wireless data communication with a mobile device comprising: an analyte sensor; a transceiver configured to transmit and receive wireless signals; and a processor operatively coupled to the analyte sensor and the transceiver and configured to: cause the transceiver to transmit a series of advertisement signals, receive a data connection request from a mobile device, cause the transceiver to establish a data connection with a radio unit of the mobile device, cause the transceiver to transmit a connection interval for use by the mobile device for calculating an exit time at which the mobile device is to exit an inactive mode and start to search for an advertisement signal, cause the transceiver to transmit an analyte value, cause the transceiver to terminate the data connection, and cause the transceiver to enter a sleep mode.

In certain implementations of the fifth aspect, which is generally applicable, particularly with any other implementation of the fifth aspect, the processor can be further configured to cause the transceiver to exit the sleep mode after a predetermined time period; and cause the transceiver to transmit a second series of advertisement signals.

In certain implementations of the fifth aspect, which is generally applicable, particularly with any other implementation of the fifth aspect, the connection interval can be a function of a difference between a first time at which the transceiver began to transmit a series of advertisement signals and a second time at which the transceiver received the data connection request from the mobile device.

In certain implementations of the fifth aspect, which is generally applicable, particularly with any other implementation of the fifth aspect, the analyte sensor can be a continuous glucose sensor.

In a sixth aspect is provided a mobile device configured for a wireless data communication with an analyte sensor system, the mobile device comprising: a memory for storing a custom application; a radio unit for transmitting and receiving wireless signals; and a processor operatively coupled to the memory and the radio unit and configured to: cause the radio unit to search for advertisement signals, receive an advertisement signal from a transceiver associated with the analyte sensor system, cause the radio unit to transmit a data connection request to the transceiver, receive a grant of the data connection request from the transceiver, cause the radio unit to establish a data connection with the transceiver, receive a connection interval indicative of an amount of time elapsed between a beginning of transmission of a series of advertisement signals by the transceiver and a reception of a data connection request by the transceiver, cause the radio unit to terminate the data connection with the transceiver, cause the radio unit to enter an inactive mode during which the radio unit does not communicate with the transceiver, calculate an exit time based at least partly on the connection interval, cause the radio unit to exit from the inactive mode at the exit time, and cause the radio unit to search for advertisement signals after exiting the inactive mode.

In certain implementations of the sixth aspect, which is generally applicable, particularly with any other implementation of the sixth aspect, the analyte sensor system can be a continuous glucose sensor system.

In certain implementations of the sixth aspect, which is generally applicable, particularly with any other implementation of the sixth aspect, the mobile device can be a mobile phone.

In certain implementations of the sixth aspect, which is generally applicable, particularly with any other implementation of the sixth aspect, the exit time can be given by current time+update interval−the connection time−notification delay−safeguard, the update interval can be a time duration between two consecutive wireless communication sessions between the transceiver and the mobile device.

In a seventh aspect is provided a method for a wireless data communication between an analyte sensor system and a plurality of display devices capable of displaying analyte values wirelessly received from the analyte sensor system, the method comprising: transmitting a first series of advertisement signals; receiving a first data connection request from a first display device; determining whether the first display device is identified in a list for containing a single allowed display device; and rejecting the first data connection request from the first display device at a radio hardware level if the first display device is not identified in the list.

In certain implementations of the seventh aspect, which is generally applicable, particularly with any other implementation of the seventh aspect, the method further comprises granting the first data connection from the first display device at the radio hardware level if the first display device is identified in the list.

In certain implementations of the seventh aspect, which is generally applicable, particularly with any other implementation of the seventh aspect, the method further comprises establishing a first data connection with the first display device and transmitting an analyte value to the first display device.

In certain implementations of the seventh aspect, which is generally applicable, particularly with any other implementation of the seventh aspect, the analyte value can be indicative a blood glucose value.

In certain implementations of the seventh aspect, which is generally applicable, particularly with any other implementation of the seventh aspect, the information identifying one or more display devices that have been paired with the transceiver can also be stored in the list.

In certain implementations of the seventh aspect, which is generally applicable, particularly with any other implementation of the seventh aspect, the information identifying one or more display devices that have been paired with the transceiver can be stored in a different list.

In certain implementations of the seventh aspect, which is generally applicable, particularly with any other implementation of the seventh aspect, the method can further comprise continuing to accept data connection requests from one or more display devices when no other display device has been paired with the analyte sensor system.

In certain implementations of the seventh aspect, which is generally applicable, particularly with any other implementation of the seventh aspect, the method can further comprise clearing the list if a predetermined condition is met.

In certain implementations of the seventh aspect, which is generally applicable, particularly with any other implementation of the seventh aspect, the predetermined condition can be a failure to receive a data connection request from a listed display device identified in the list within a predetermined number of communication sessions.

In certain implementations of the seventh aspect, which is generally applicable, particularly with any other implementation of the seventh aspect, the predetermined condition can be reception of a clearance signal from a listed display device identified in the list indicating that the listed display device is to be cleared from the list.

In certain implementations of the seventh aspect, which is generally applicable, particularly with any other implementation of the seventh aspect, the method can further comprise receiving a second data connection request from a second display device; determine that the list has been cleared; grant the second data connection request; and write data identifying the second display device in the list.

In an eighth aspect is provided an analyte sensor system configured for a wireless data communication with a plurality of display devices capable of displaying analyte values wirelessly received from the analyte sensor system, the analyte sensor system comprising: an analyte sensor; a memory for storing a list identifying a single allowed display device; a transceiver configured to transmit and receive wireless signals; and a processor operatively coupled to the analyte sensor, the memory, and the transceiver and configured to: cause the transceiver to transmit a first series of advertisement signals, receive a first data connection request from a first display device, determine that the first display device is not identified in the list, and reject the data connection request from the first display device at a radio hardware level.

In certain implementations of the eighth aspect, which is generally applicable, particularly with any other implementation of the eighth aspect, the analyte sensor can be a continuous glucose sensor.

In certain implementations of the eighth aspect, which is generally applicable, particularly with any other implementation of the eighth aspect, one of the plurality of display devices can be a custom analyte monitoring device and another one of the plurality of display devices is a mobile device.

In certain implementations of the eighth aspect, which is generally applicable, particularly with any other implementation of the eighth aspect, the wireless data communication can employ a short-distance and low-power wireless communication protocol.

In certain implementations of the eighth aspect, which is generally applicable, particularly with any other implementation of the eighth aspect, the processor can be a link layer (LL) controller.

In certain implementations of the eighth aspect, which is generally applicable, particularly with any other implementation of the eighth aspect, the list can be a white list maintained in the LL controller.

In certain implementations of the eighth aspect, which is generally applicable, particularly with any other implementation of the eighth aspect, the processor can be further configured to cause the transceiver to continue transmitting one or more advertisement signals after rejecting the first data connection request, receive a data connection request from a second display device, and establish a data connection with the second display device if the second display device is identified in the list.

In certain implementations of the eighth aspect, which is generally applicable, particularly with any other implementation of the eighth aspect, the processor can be further configured to engage in data communication with the second display device after establishing the data connection, terminate the data connection after completing the data communication, and cause the transceiver to enter a sleep mode.

In certain implementations of the eighth aspect, which is generally applicable, particularly with any other implementation of the eighth aspect, the processor can be further configured to clear the list if a predetermined condition is met.

In certain implementations of the eighth aspect, which is generally applicable, particularly with any other implementation of the eighth aspect, the predetermined condition can include a failure to receive a data connection request from a listed display device identified in the list within a predetermined number of communication sessions.

In certain implementations of the eighth aspect, which is generally applicable, particularly with any other implementation of the eighth aspect, the predetermined condition includes a reception of a clearance signal from a listed display device can be identified in the list indicating that the listed display device is to be cleared from the list.

In certain implementations of the eighth aspect, which is generally applicable, particularly with any other implementation of the eighth aspect, the processor can be further configured to receive a second data connection request from a second display device, determine that the list has been cleared, cause the transceiver to grant the second data connection request, and write data identifying the second display device in the list. In a ninth aspect is provided a method for a wireless data communication between an analyte sensor system and a plurality of display devices capable of displaying analyte values wirelessly received from the analyte sensor system, the method comprising: transmitting a first series of advertisement signals; receiving a first data connection request from a first display device; determining that the first display device is identified in a first list containing one or more allowed display devices; establishing a first data connection with the first display device; transmitting a first signal to the first display device indicating that a different display device is identified in a second list for containing a single currently active display device; receiving a second signal from the first display device indicating that the first display device is a newly selected active display device; changing the second list to indicate that the first display device is the currently active display device; and terminating the first data connection with the first display device.

In certain implementations of the ninth aspect, which is generally applicable, particularly with any other implementation of the ninth aspect, the method can further comprise determining that the first display device is not identified in the second list.

In certain implementations of the ninth aspect, which is generally applicable, particularly with any other implementation of the ninth aspect, the method can further comprise receiving a request from the first display device to transmit the first signal.

In certain implementations of the ninth aspect, which is generally applicable, particularly with any other implementation of the ninth aspect, the method can further comprise reading from the second list first data identifying the different display device as the currently active display device; and including the first data in the first signal transmitted to the first display device.

In certain implementations of the ninth aspect, which is generally applicable, particularly with any other implementation of the ninth aspect, the second signal can comprise a request to write to the second list second data identifying the first display device as the currently active display device.

In certain implementations of the ninth aspect, which is generally applicable, particularly with any other implementation of the ninth aspect, the method can be further comprised transmitting a second series of advertisement signals; receiving a second data connection request from the first display device; establishing a second data connection with the first display device; determining that the first display device is identified in the second list; transmitting an analyte value to the first display device; and terminating the second data connection with the first display device.

In certain implementations of the ninth aspect, which is generally applicable, particularly with any other implementation of the ninth aspect, the method can be further comprised transmitting a third series of advertisement signals; receiving a third data connection request from a second display device; establishing a third data connection with the second display device if it is determined that the second display device is identified in the first list; transmitting a third signal to the second display indicating that a different display device is identified in the second list; receiving a fourth signal from the second display device, the fourth signal indicating that the third display device is not a newly selected active display device; and terminating the third data connection with the second display device without changing the second list.

In a tenth aspect is provided an analyte sensor system configured for a wireless data communication with a plurality of display devices capable of displaying analyte values from the analyte sensor module, the analyte sensor system comprising: an analyte sensor; a transceiver configured to transmit and receive wireless signals; and a processor operatively coupled to the analyte sensor, and the transceiver and configured to: cause the transceiver to transmit a first series of advertisement signals, receive a first data connection request from a first display device, determine that the first display device is identified in a first list containing one or more allowed display devices, establish a first data connection with the first display device, read from a second list first data identifying a different display device as a currently active display device, transmit the first data to the first display device, receive a request to write to the second list second data identifying the first display device as a currently active display device, write the second data to the second list, and terminate the first data connection with the first display device.

In certain implementations of the tenth aspect, which is generally applicable, particularly with any other implementation of the tenth aspect, the analyte sensor can be a continuous glucose sensor.

In certain implementations of the tenth aspect, which is generally applicable, particularly with any other implementation of the tenth aspect, at least one of the first display device and the different display device can be a custom analyte monitoring device and the other of the first display device and the different display device is a mobile device.

In certain implementations of the tenth aspect, which is generally applicable, particularly with any other implementation of the tenth aspect, the mobile device can be a mobile phone.

In certain implementations of the tenth aspect, which is generally applicable, particularly with any other implementation of the tenth aspect, the processor can be configured to reject a data connection request from a display device not identified in the first list at a radio hardware level.

In certain implementations of the tenth aspect, which is generally applicable, particularly with any other implementation of the tenth aspect, the processor can comprise a link layer (LL) controller.

In certain implementations of the tenth aspect, which is generally applicable, particularly with any other implementation of the tenth aspect, the first list can be a white list maintained in the LL controller.

In certain implementations of the tenth aspect, which is generally applicable, particularly with any other implementation of the tenth aspect, the processor can be further configured to cause the transceiver to transmit a second series of advertisement signals, receive a second data connection request from the first display device, cause the transceiver to establish a second data connection with the first display device, determine that the first display device is identified in the second list, cause the transceiver to transmit an analyte value to the first display device, and cause the transceiver to terminate the second data connection with the first display device.

In certain implementations of the tenth aspect, which is generally applicable, particularly with any other implementation of the tenth aspect, the processor can be further configured to cause the transceiver to enter a sleep mode; and cause the transceiver to exit the sleep mode after a predetermined time.

In certain implementations of the tenth aspect, which is generally applicable, particularly with any other implementation of the tenth aspect, the predetermined time can be between about 200 and 300 seconds.

In certain implementations of the tenth aspect, which is generally applicable, particularly with any other implementation of the tenth aspect, the processor can be further configured to take a measurement of an output of the analyte sensor while the transceiver is in the sleep mode.

In certain implementations of the tenth aspect, which is generally applicable, particularly with any other implementation of the tenth aspect, processor can be further configured to cause the transceiver to transmit a third series of advertisement signals after exiting, receive a third data connection request from a second display device, cause the transceiver to establish a third data connection with the second display device if it is determined that the second display device is identified in the first list, cause the transceiver to transmit a third signal to the second display indicating that a different display device is identified in the second list, receive a fourth signal from the second display device, the fourth signal indicating that the third display device is not a newly selected active display device, and cause the transceiver to terminate the third data connection with the second display device without changing the second list.

In a eleventh aspect is provided a method for wireless data communication among an analyte sensor system, a passive device for receiving data from the transceiver without establishing a data connection with the analyte sensor system, and an active display device for displaying analyte data from the analyte sensor system after establishing a data connection with the analyte sensor system, the method comprising: the passive device receiving a first advertisement signal from the analyte sensor system, the first advertisement signal including data to be used by the passive device; and the passive device extracting the data from the first advertisement signal.

In certain implementations of the eleventh aspect, which is generally applicable, particularly with any other implementation of the eleventh aspect, the data can be included in the first advertisement signal includes an analyte value.

In certain implementations of the eleventh aspect, which is generally applicable, particularly with any other implementation of the eleventh aspect, the analyte value can be an encoded analyte value.

In certain implementations of the eleventh aspect, which is generally applicable, particularly with any other implementation of the eleventh aspect, the method can further comprise the active display device receiving a second advertisement signal from the transceiver; the active display device establishing a data connection with the transceiver in response to the second advertisement signal; and the active display device receiving an analyte value to be displayed on the active display device.

In certain implementations of the eleventh aspect, which is generally applicable, particularly with any other implementation of the eleventh aspect, the second advertisement signal can be same as the first advertisement signal.

In certain implementations of the eleventh aspect, which is generally applicable, particularly with any other implementation of the eleventh aspect, the second advertisement signal can be different from the first advertisement signal.

In a twelfth aspect is provided a system for wireless data communication comprising: an analyte sensor system configured to transmit a series of advertisement signals; a passive device configured to: receive a first advertisement signal from the analyte sensor system, the first advertisement signal being one of the series of advertisement signals transmitted by the analyte sensor system and including data to be used by the passive device, and extract the data from the first advertisement signal without establishing a data connection with the analyte sensor system; and an active display device configured to: receive a second advertisement signal from the analyte sensor system, the second advertisement signal being one of the series of advertisement signals transmitted by the analyte sensor system, establish a data connection with the analyte sensor system in response to the second advertisement signal, receive an analyte value from the analyte sensor system, terminate the data connection, and display the analyte value.

In certain implementations of the twelfth aspect, which is generally applicable, particularly with any other implementation of the twelfth aspect, the data to be used by the passive device can include an encoded analyte value.

In certain implementations of the twelfth aspect, which is generally applicable, particularly with any other implementation of the twelfth aspect, the analyte sensor system can be a continuous glucose sensor system and the passive device is an insulin pump configured for insulin administration.

In certain implementations of the twelfth aspect, which is generally applicable, particularly with any other implementation of the twelfth aspect, the data included in the first advertisement signal can be indicative of a glucose level and further wherein the insulin pump is configured to suspend the insulin administration if the glucose level falls below a threshold value.

Any of the features of aspects specified herein are applicable to all other aspects and embodiments identified herein. Moreover, any of the features of an aspect is independently combinable, partly or wholly with other aspects described herein in any way, e.g., one, two, or three or more aspects may be combinable in whole or in part. Further, any of the features of an aspect may be made optional to other aspects. Any aspect of a method can be performed by a system or apparatus of another aspect, and any aspect or of a system can be configured to perform a method of another aspect.

DETAILED DESCRIPTION

Figure 1:
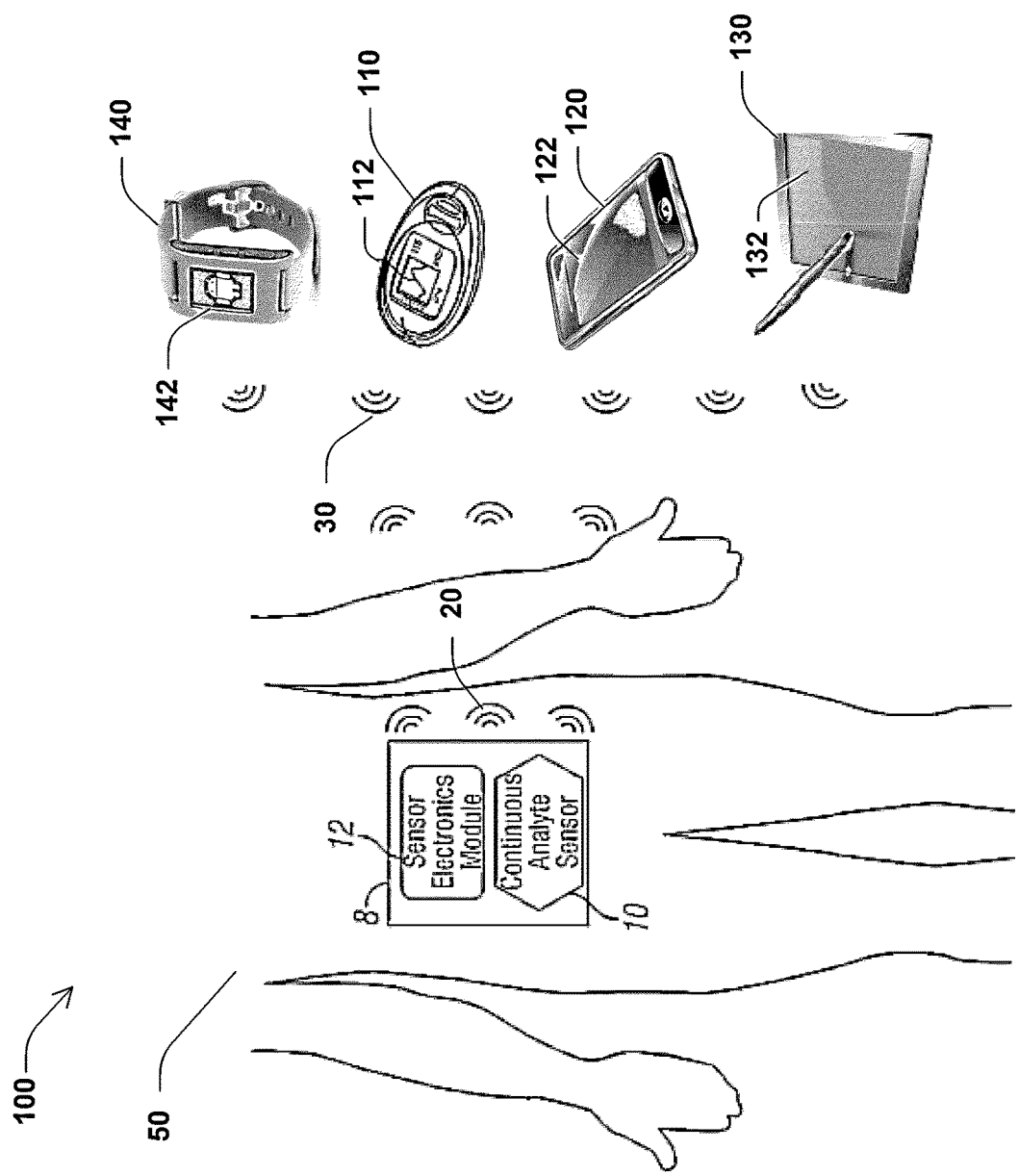
FIG. 1 is a diagram illustrating certain embodiments of a continuous analyte sensor system according certain aspects of the present disclosure.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Overview

In some embodiments, a system is provided for continuous measurement of an analyte in a host that includes: a continuous analyte sensor configured to continuously measure a concentration of the analyte in the host and a sensor electronics module physically connected to the continuous analyte sensor during sensor use. In certain embodiments, the sensor electronics module includes electronics configured to process a data stream associated with an analyte concentration measured by the continuous analyte sensor in order to generate sensor information that includes raw sensor data, transformed sensor data, and/or any other sensor data, for example. The sensor electronics module may further be configured to generate sensor information that is customized for respective display devices, such that different display devices may receive different sensor information.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A−1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Alerts

In certain embodiments, one or more alerts are associated with a sensor electronics module. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g. an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In certain embodiments, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In certain embodiments, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. Co-pending U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data package indicating an alarm should be initiated by one or a plurality of display devices (e.g., sequentially and/or simultaneously). In certain embodiments, the sensor electronics module merely provides a data field indicating that an alarm conditions exists and the display device, upon reading the data field indicating the existence of the alarm condition, may decide to trigger an alarm. In some embodiments, the sensor electronics module determines which of the one or more alarms to trigger based on one or more alerts that are triggered. For example, when an alert trigger indicates severe hypoglycemia, the sensor electronics module can perform multiple actions, such as activating an alarm on the sensor electronics module, transmitting a data package to a monitoring device indicating activation of an alarm on the display, and transmitting a data package as a text message to a care provider. As an example, a text message can appear on a custom monitoring device, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one exemplary embodiment, the sensor electronics module is configured to search for and attempt to alarm a host or care provider sequentially using a list of display devices, such as: 1) a default display device or a custom analyte monitoring device, 2) a mobile phone via auditory and/or visual methods, such as, text message to the host and/or care provider, voice message to the host and/or care provider, and/or 911), 3) a tablet, 4) a smart watch.

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may comprise software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, tablets, PDAs, PCs and the like).

In some embodiments, certain display devices may be in direct wireless communication with the sensor electronics module, however intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In certain embodiments, the sensor electronics module directly wirelessly transmits displayable sensor information to one or a plurality of display devices, such that the displayable sensor information transmitted from the sensor electronics module is received by the display device without intermediate processing of the displayable sensor information.

In certain embodiments, one or more display devices comprise built-in authentication mechanisms, wherein authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password.

In some embodiments, one or more display devices are configured to query the sensor electronics module for displayable sensor information, wherein the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how they obtain sensor information.

In some embodiments, as described in more detail elsewhere herein, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with embodiments disclosed herein.

In general, a plurality of display devices (e.g., a custom analyte monitoring device, a mobile phone, a tablet, a smart watch, a reference analyte monitor, a drug delivery device, a medical device and a personal computer) are configured to wirelessly communicate with the sensor electronics module, wherein the one or more display devices are configured to display at least some of the displayable sensor information wirelessly communicated from the sensor electronics module, wherein displayable sensor information includes sensor data, such as raw data and/or transformed sensor data, such as analyte concentration values, rate of change information, trend information, alert information, sensor diagnostic information and/or calibration information, for example.

Exemplary Configurations

FIG. 1 is a diagram depicting an exemplary continuous analyte monitoring system 100 including an analyte sensor system 8 and a plurality of display devices 110, 120, 130, 140 according to certain aspects of the present disclosure. The analyte sensor system 8 includes a sensor electronics module 12 and a continuous analyte sensor 10 associated with the sensor electronics module 12. The sensor electronics module 12 is in direct wireless communication with one or more of the plurality of display devices 110, 120, 130, and/or 140 shown.

In certain embodiments, the sensor electronics module 12 includes electronic circuitry associated with measuring and processing the continuous analyte sensor data, including prospective algorithms associated with processing and calibration of the sensor data. The sensor electronics module 12 can be physically connected to the continuous analyte sensor 10 and can be integral with (non-releasably attached to) or releasably attachable to the continuous analyte sensor 10. The sensor electronics module 12 may include hardware, firmware, and/or software that enables measurement of levels of the analyte via a glucose sensor. For example, the sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The sensor electronics module 12 includes sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Referring again to FIG. 1, the plurality of display devices (110, 120, 130, and/or 140) are configured for displaying (and/or alarming) the displayable sensor information that has been transmitted by the sensor electronics module 12 (e.g., in a customized data package that is transmitted to the display devices based on their respective preferences). Each of the display devices 110, 120, 130, or 140 can include a display such as a touchscreen display 112, 122, 132, or 142 for displaying sensor information to a user and/or receiving inputs from the user. In some embodiments, the display devices may include other types of user interfaces such as voice user interface instead of or in addition to a touchscreen display for communicating sensor information to the user of the display device and/or receiving user inputs. In some embodiments, one, some or all of the display devices is configured to display or otherwise communicate the sensor information as it is communicated from the sensor electronics module (e.g., in a data package that is transmitted to respective display devices), without any additional prospective processing required for calibration and real-time display of the sensor data.

In the embodiment of FIG. 1, the plurality of display devices includes a custom display device 110 specially designed for displaying certain types of displayable sensor information associated with analyte values received from the sensor electronics module 12 (e.g., a numerical value and an arrow, in some embodiments). In some embodiments, one of the plurality of display devices is a mobile phone 120 based on an Android or iOS operating system, a palm-top computer and/or the like, wherein the display device comprises a relatively larger display and is configured to display a graphical representation of the continuous sensor data (e.g., including current and historic data). Other display devices can include other hand-held devices, such as a tablet 130, a smart watch 140, an insulin delivery device, a blood glucose meter, and/or a desktop or laptop computer.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1, a plurality of different display devices can be in direct wireless communication with the sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

Continuous Sensor

In some embodiments, analyte sensor 10 of FIG. 1 comprises a continuous glucose sensor, for example a subcutaneous, transdermal (e.g., transcutaneous), or intravascular device. In some embodiments, the device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

In certain embodiments, the analyte sensor is an implantable glucose sensor, such as described with reference to U.S. Pat. No. 6,001,067 and U.S. Patent Publication No. US-2005-0027463-A1. In another embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, co-pending U.S. Patent Publication No. US-2008-0108942-A1 filed on Mar. 26, 2007, and co-pending U.S. Patent Application No. US-2007-0197890-A1 filed on Feb. 14, 2007. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al., for example.

Figure 2A:
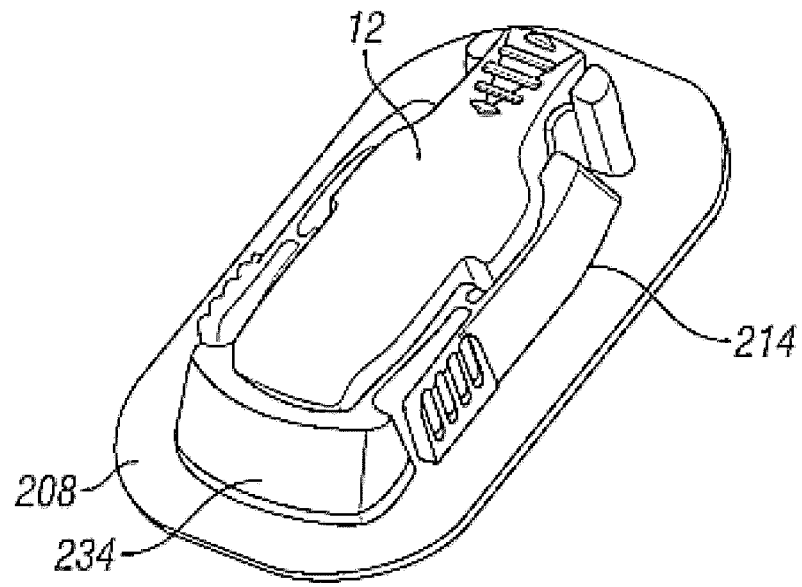
FIG. 2A is a perspective view of an exemplary sensor system that can embody the analyte sensor system according to certain aspects of the present disclosure.
Figure 2B:
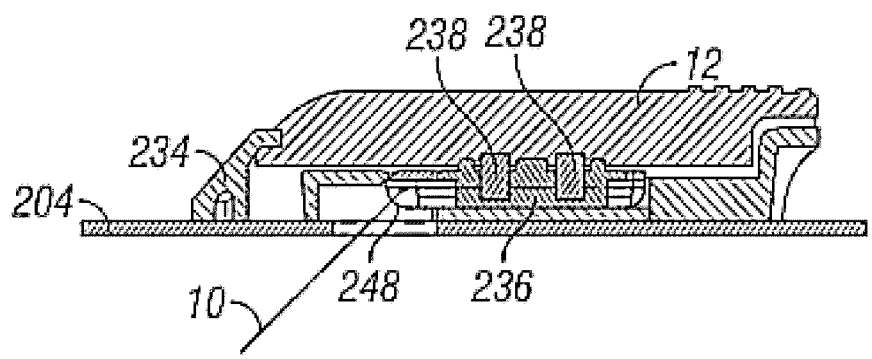
FIG. 2B is a side view of an exemplary sensor system that can embody the analyte sensor system according to certain aspects of the present disclosure.

FIGS. 2A and 2B are perspective and side views of an exemplary sensor system that can incorporate the analyte sensor system 8 shown in FIG. 1 according certain aspects of the present disclosure. The sensor system includes a mounting unit 214 and sensor electronics module 12 attached thereto in certain embodiments, shown in its functional position, including a mounting unit and a sensor electronics module matingly engaged therein. In some embodiments, the mounting unit 214, also referred to as a housing or sensor pod, comprises a base 234 adapted for fastening to a host's skin. The base can be formed from a variety of hard or soft materials, and can comprises a low profile for minimizing protrusion of the device from the host during use. In some embodiments, the base 234 is formed at least partially from a flexible material, which is believed to provide numerous advantages over conventional transcutaneous sensors, which, unfortunately, can suffer from motion-related artifacts associated with the host's movement when the host is using the device. The mounting unit 214 and/or sensor electronics module 12 can be located over the sensor insertion site to protect the site and/or provide a minimal footprint (utilization of surface area of the host's skin).

In some embodiments, a detachable connection between the mounting unit 214 and sensor electronics module 12 is provided, which enables improved manufacturability, namely, the relatively inexpensive mounting unit 214 can be disposed of when replacing the sensor system after its usable life, while the relatively more expensive sensor electronics module 12 can be reusable with multiple sensor systems. In some embodiments, the sensor electronics module 12 is configured with signal processing (programming), for example, configured to filter, calibrate and/or other algorithms useful for calibration and/or display of sensor information. However, an integral (non-detachable) sensor electronics module can be configured.

In some embodiments, the contacts 238 are mounted on or in a subassembly hereinafter referred to as a contact subassembly 236 configured to fit within the base 234 of the mounting unit 214 and a hinge 248 that allows the contact subassembly 236 to pivot between a first position (for insertion) and a second position (for use) relative to the mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, the contacts 238 are formed from a conductive elastomeric material, such as a carbon black elastomer, through which the sensor 10 extends.

In certain embodiments, the mounting unit 214 is provided with an adhesive pad 208, disposed on the mounting unit's back surface and includes a releasable backing layer. Thus, removing the backing layer and pressing the base portion 234 of the mounting unit onto the host's skin adheres the mounting unit 214 to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Patent Publication No. US-2009-0240120-A1, which is incorporated herein by reference in its entirety for all purposes.

Figure 3:
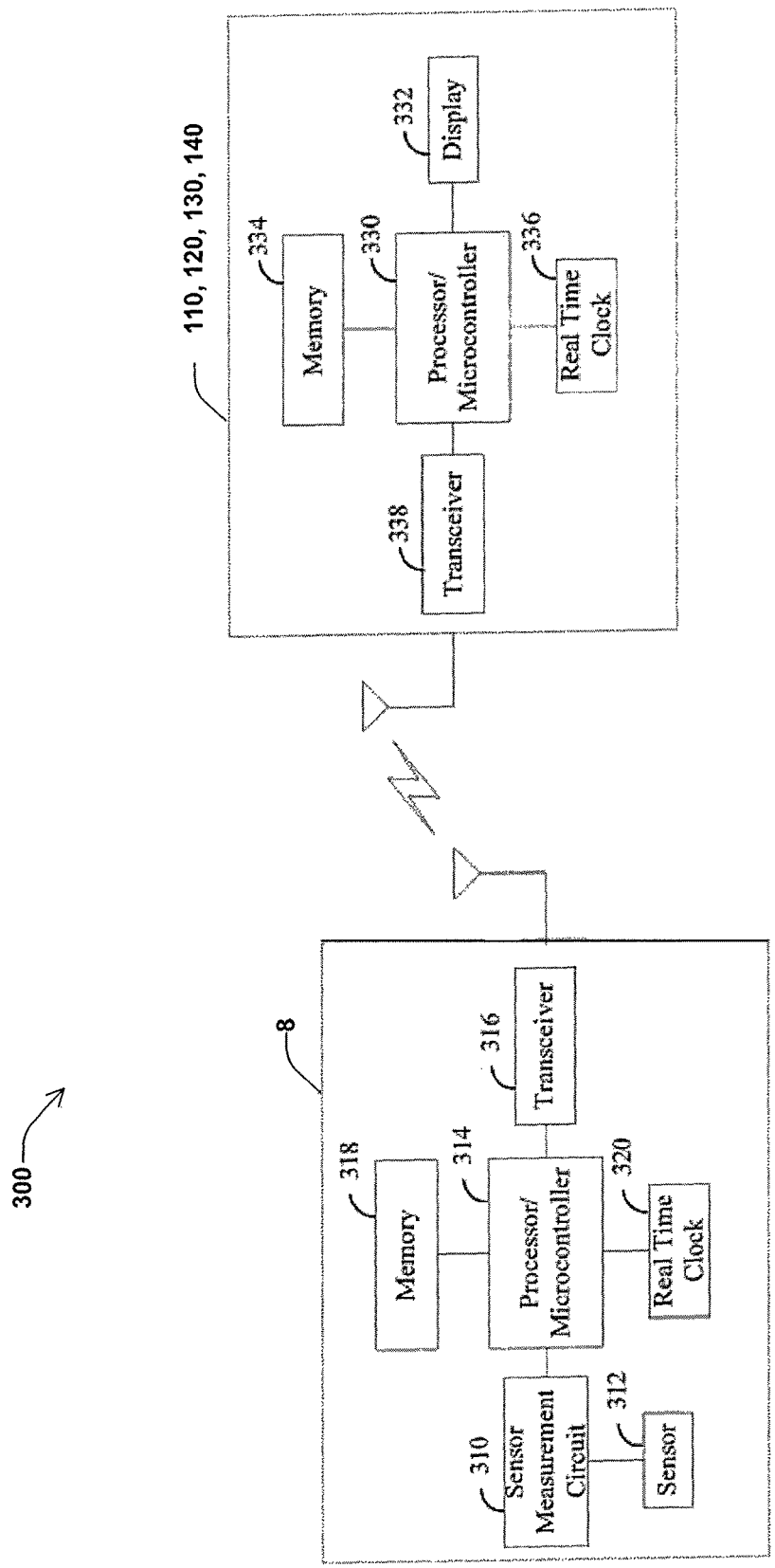
FIG. 3 is an exemplary block diagram illustrating various elements of certain embodiments of a continuous analyte monitoring system comprising an analyte sensor system and a plurality of display devices according to certain aspects of the present disclosure.

FIG. 3 is an exemplary block diagram illustrating various elements of certain embodiments of a continuous analyte monitoring system 300 comprising analyte sensor system 8 and display devices 110, 120, 130, 140. The analyte sensor system 8 may include an analyte sensor 312 (also designated 10 in FIG. 1) coupled to a sensor measurement circuit 310 for processing and managing sensor data. The sensor measurement circuit 310 may be coupled to a processor 314 (part of item 12 in FIG. 1). In some embodiments, the processor 314 may perform part or all of the functions of the sensor measurement circuit 310 for obtaining and processing sensor measurement values from the sensor 312. The processor may be further coupled to a radio unit or transceiver 316 (part of item 12 in FIG. 1) for sending sensor data and receiving requests and commands from an external device, such as the display device 110, 120, 130, 140, which is used to display or otherwise provide the sensor data to a user. As used herein, the terms "radio unit" and "transceiver" are used interchangeably and generally refer to a device that can wirelessly transmit and receive data. The analyte sensor system 8 may further include a memory 318 (part of item 12 in FIG. 1) and a real time clock (RTC) 320 (part of item 12 in FIG. 1) for storing and tracking sensor data.

Wireless communication protocols may be used to transmit and receive data between the sensor system 8 and the display device 110, 120, 130, 140. The wireless protocol used may be designed for use in a wireless sensor network that is optimized for periodic and small data transmissions (that may be transmitted at low rates if necessary) to and from multiple devices in a close range (e.g., a personal area network (PAN)). For example, the protocol may be optimized for periodic data transfers where transceivers may be configured to transmit data for short intervals and then enter low power modes for long intervals. The protocol may have low overhead requirements both for normal data transmissions and for initially setting up communication channels (e.g., by reducing header overhead) to reduce power consumption. In some embodiments, burst broadcasting schemes (e.g., one way communication) may be used. This may eliminate overhead required for acknowledgement signals and allow for periodic transmissions that consume little power.

The protocol may further be configured to establish communication channels with multiple devices while implementing interference avoidance schemes. In some embodiments, the protocol may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA) based schemes. The wireless protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as WiFi, Bluetooth and Bluetooth Low Energy (BLE). The wireless protocol may operate in various frequency bands such as an open ISM band such as 2.4 GHz. Furthermore, to reduce power usage, the wireless protocol may adaptively configure data rates according to power consumption.

The display device 110, 120, 130, 140 may be used for alerting and providing sensor information to a user, and may include a processor 330 for processing and managing sensor data. The display device 110, 120, 130, 140 may include a display 332, a memory 334, and a real time clock 336 for displaying, storing and tracking sensor data respectively. The display device 110, 120, 130, 140 may further include a radio unit or transceiver 338 for receiving sensor data and for sending requests, instructions, and data to the analyte sensor system 8. The transceiver 338 may further employ a communication protocol. The memory 334 may also be used for storing an operating system for the display device and/or a custom (e.g., proprietary) application designed for wireless data communication between a transceiver and the display device. The memory 334 may be a single memory device or multiple memory devices and may be a volatile or non-volatile memory for storing data and/or instructions for software programs and applications. The instructions may be executed by the processor 330 to control and manage the transceiver 338.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, the processor 314, 330 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver circuit 316.

Components of the analyte sensor system 8 may require replacement periodically. For example, the analyte sensor system 8 may include an implantable sensor 312 that may be attached to a sensor electronics module that includes the sensor measurement circuit 310, the processor 314, memory 318, and transceiver 316, and battery (not shown). The sensor 312 may require periodic replacement (e.g., every 7-30 days). The sensor electronics module may be configured to be powered and active for much longer than the sensor 312 (e.g., for three, six months or more) until the battery needs replacement. Replacing these components may be difficult and require the assistance of trained personnel. Reducing the need to replace such components, particularly the battery, significantly improves the convenience of the analyte sensor system 8 to the user. In some embodiments, the sensor session as defined above may correspond to the life of the sensor 312 (e.g., in the range of 7 to 30 days). When a sensor electronic module is used for the first time (or reactivated once a battery has been replaced in some cases), it may be connected to a sensor 312 and a sensor session may be established. As will be further described below, there may be a process for initially establishing communication between a display device 110, 120, 130, 140 and the sensor electronics module when it is first used or re-activated (e.g., the battery is replaced). Once the display device 110, 120, 130, 140 and sensor electronics module have established communication, the display device 110, 120, 130, 140 and sensor electronics module may periodically and/or continuously be in communication over the life of several sensors 312 until, for example, the battery needs to be replaced. Each time a sensor 312 is replaced, a new sensor session may be established. The new sensor session may be initiated through a process completed using a display device 110, 120, 130, 140 and the process may be triggered by notifications of a new sensor via the communication between the sensor electronics module and the display device 110, 120, 130, 140 that may be persistent across sensor sessions.

The analyte sensor system 8 gathers analyte data from the sensor 312 that it periodically sends to the display device 110, 120, 130, 140. Data points are gathered and transmitted over the life of the sensor (e.g., in the range of 1 to 30 days or more). New measurements may need to be transmitted often enough to adequately monitor glucose levels. Rather than having the transmission and receiving circuitry of each of the sensor system 8 and display device 110, 120, 130, 140 continuously communicating, the analyte sensor system 8 and display device 110, 120, 130, 140 may regularly and periodically establish a communication channel between them. Thus, sensor system 8 can communicate via wireless transmission with display device 110, 120, 130, 140 (e.g., a hand-held computing device) at predetermined time intervals. The duration of the predetermined time interval can be selected to be long enough so that the sensor system 8 does not consume too much power by transmitting data more frequently than needed, yet frequent enough to provide substantially real-time sensor information (e.g., measured glucose values) to the display device 110, 120, 130, 140 for output (e.g., display) to a user. While the predetermined time interval is every five minutes in some embodiments, it is appreciated that this time interval can be varied to be any desired length of time.

Figure 4:
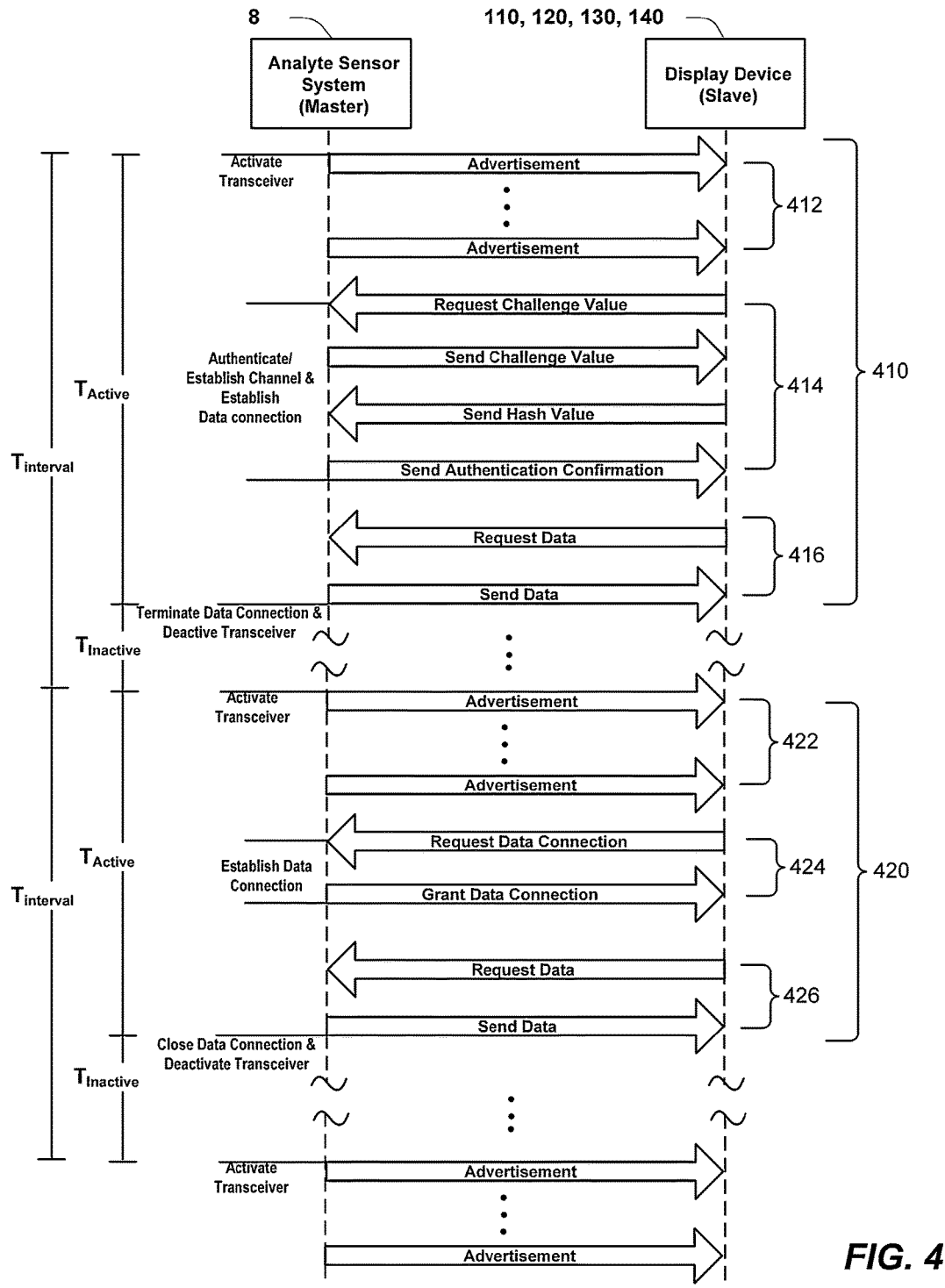
FIG. 4 is a flow diagram illustrating an exemplary wireless data communication procedure between an analyte sensor system and a display device capable of wireless receiving analyte values from the analyte sensor system according to certain aspects of the present disclosure.

FIG. 4 is a flow diagram illustrating an exemplary wireless data communication procedure between an analyte sensor system 8 and a display device 110, 120, 130, 140 capable of wirelessly receiving analyte values from the analyte sensor system 8 according to certain aspects of the present disclosure. The various tasks performed in connection with the procedure illustrated in FIG. 4 may be performed by a processor executing instructions embodied in non-transitory computer-readable medium. For example, the tasks performed in connection with the procedure may be performed by hardware, software, firmware, or any combination thereof incorporated into one or more of computing devices, such as one or more of sensor system 8 and display devices 110, 120, 130 and 140 of FIG. 1 and/or FIG. 3. It should be appreciated that the procedure may include any number of additional or alternative tasks. The tasks shown in FIG. 4 need not be performed in the illustrated order, and the procedure may be incorporated into a more comprehensive procedure or process having additional functionality not described in detail herein.

In the example described below, the analyte values are glucose values based on one or more measurements of glucose level by the analyte sensor 312 for illustration purposes. However, it should be understood that the analyte values can be any other analyte value described herein. The wireless data communication between the analyte sensor system 8 and the display device may happen periodically, at times separated by an update interval denoted "$T_{interval}$" that may correspond to a time duration between two consecutive wireless communication sessions between the transceiver 316 of the analyte sensor system 8 and the transceiver 338 of the display device 110, 120, 130, 140. Alternatively, the update interval may be thought of as a period of obtaining and sending a recently measured glucose value. Transmitting advertisement signals, establishing a data connection (e.g., a communication channel) and requesting and sending data may occur during wireless communication sessions each lasting an active time or period denoted "$T_{Active}$" within an update interval $T_{interval}$. In between two consecutive wireless communication sessions, the transceiver 316 goes into an inactive or sleep mode for an inactive period denoted as "$T_{Inactive}$" to conserve battery life and/or reduce peak voltage requirements, for example.

FIG. 4 shows two such wireless communication sessions, namely, a first wireless communication session 410 and a second wireless communication session 420. Each wireless communication session 410, 420 starts with the analyte sensor system 8 establishing a data connection with a display device 110, 120, 130, 140. To establish a data connection with the display device 110, 120, 130, 140, the transceiver 316 of the analyte sensor system 8 transmits a series of advertisement signals 412 during the first wireless communication session 420. Each advertisement signal may be considered an invitation for a display device 110, 120, 130, 140 to establish a data connection with the transceiver 316.

In the illustrated example of FIG. 4, it is assumed that the analyte sensor system 8 needs to engage in an initial system setup because the system 8 has been just turned on for the first time and/or is currently not paired with a display device 110, 120, 130, 140. Typically, a user of the display device 110, 120, 130, 140 identifies a new or never-been used analyte sensor system 8 that needs to be paired with the display device by entering identification information (e.g., a serial number) associated with the new/unpaired analyte sensor system 8 via a custom application running on the display device using a user interface (e.g., a touchscreen display). During the first wireless communication session 410, an authentication procedure needs to be performed as part of a data connection process 414. To establish a data connection with the analyte sensor system 8, the display device 110, 120, 130, 140 listens continuously until an advertisement signal transmitted by the transceiver 316 of the analyte sensor system 8 is received. Once the transceiver 316 begins transmitting advertisement signals 412, it may take one, two, or more advertisement signals for the display device 110, 120, 130, 140 to receive the advertisement signal and responds to the advertisement signal. In some embodiments, the transceiver 316 stops sending additional advertisement signals once a display device receives an advertisement signal and responds to the advertisement signal, for example, via an acknowledgement. In other embodiments, the transceiver 316 may continue to send additional advertisement signals even after receiving a response from a display device so that another display device may receive and respond to one of the additional advertisement signals.

After an advertisement signal is successfully received by a display device 110, 120, 130, 140, the display device and the analyte sensor system 8 engage in a first data connection process 414. During the first data connection process 414, the display device requests a challenge value from the analyte sensor system 8 and the analyte sensor system 8 sends the change value to the display device in response. Upon receiving the challenge value, the display device calculates a hash value based on the challenge value and the identification information associated with the analyte sensor system 8 and/or the transceiver 316 and sends the hash value to the transceiver 316. The transceiver 316 receives the hash value from the display device 110, 120, 130, 140, decodes the identification information from the hash value, and verifies that the received identification information matches identification information associated with the sensor system 8 and/or transceiver 316 previously stored in the memory 318 of the analyte sensor system 8, such as during manufacturing of the sensor system 8. Upon verification, the transceiver 316 sends a signal confirming a successful authentication to the display device 110, 120, 130, 140. Once authenticated, the analyte sensor system 8 and display device 110, 120, 130, 140 may exchange information to determine how data will be exchanged (e.g., a specific frequency, time slot assignment, encryption, etc.).

After completion of the first data connection process 414, the analyte sensor system 8 and the connected display device 110, 120, 130, 140 engage in a first data communication 416 during which the connected display device requests and receives desired information (e.g., analyte data, control information, identification information, and/or instruction) from the analyte sensor system 8. When the first data communication 416 is completed, the data connection is terminated (e.g., by closing the established communication channel) and the transceiver 316 and/or the processor 314 of the analyte sensor system 8 (and possibly the transceiver 338 and/or the processor 330 of the display device 110, 120, 130, 140 as well, depending on implementation preference) can be deactivated by causing the transceiver 316 and/or the processor 314 to enter a sleep or inactive mode. In some embodiments, the transceiver 316 is completely powered down during a sleep mode. In other embodiments, the transceiver 316 is in a low power mode using only a small fraction (e.g., 1-10%) of the normal current/power.

The active period $T_{Active}$ corresponding to a duration of each wireless communication session may be a small fraction of the update interval $T_{interval}$ corresponding to a period between two consecutive wireless communication sessions. For example, $T_{interval}$ may be between about 200 and 400 seconds and $T_{Active}$ may be between 20 and 40 seconds. As such, the transceiver 316 of the analyte sensor system 8 may be powered fully for only 10 percent (e.g., 30 seconds) of a five minute $T_{interval}$. This may significantly reduce power consumption and peak voltage demand. In some cases, the transceiver 316 is not completely powered down, but enters a low-power mode when not transmitting. After an inactive time or period $T_{Inactive}$, a second wireless communication session 420 starts when the transceiver 316 (and the transceiver 338) powers up again, begins transmitting a second series of advertisement signals 422, engages in a second data connection process 424 and a second data communication process 426 with the transceiver 338 of the display device 110, 120, 130, 140 as shown in FIG. 4. Unlike the first data connection process 414, however, the second data connection process 424 does not involve an authentication because the analyte sensor system 8 and the display device 110, 120, 130, 140 have been successfully paired or bonded during the first wireless communication session 410 as described above. This process may continue, with new data connections and communications being completed at the predetermined intervals. During all or part of each inactive period $T_{Inactive}$ during which the transceiver 316 is in a sleep mode, the processor 314 can take measurement(s) of one or more analyte values using the analyte sensor 312 and the sensor measurement circuitry 310. For example, the processor 314 may take multiple analyte value measurements and average them to generate a single averaged analyte value to be transmitted in a next wireless communication session.

Continuously re-establishing a new communication channel to allow for partially or wholly powering down the transceiver 316 during each update interval $T_{interval}$ can provide significant power savings and can allow the sensor electronics module 12 (FIG. 1) to operate continuously for six months or more without requiring a battery replacement. Furthermore, rather than blindly transmitting glucose data points during the update interval $T_{interval}$, establishing specific data connections (e.g., communication channels) with only the desired display devices 110, 120, 130, 140 can prevent unauthorized use and interception of glucose measurement values. In some embodiments, only a subset of multiple display devices 110, 120, 130, 140 can be configured to receive different data such as glucose measurement values and/or alarm conditions. This has a benefit of preventing multiple display devices from issuing alarms, thereby confusing and/or frustrating the user. In addition, by establishing a secure two-way communication channel, requests for specific glucose measurement values or communication of calibration or configuration information may be transmitted on an as-needed/requested basis between the analyte sensor system 8 and display device 110, 120, 130, 140.

Also, in some embodiments, the transceiver 316 may not be activated for data communication every update interval $T_{interval}$. Instead, the transceiver 316 may be activated every second, third or fourth update interval $T_{interval}$, for example, so that communication between the sensor system 8 with the display device 110, 120, 130, 140 occurs less frequently than every update interval $T_{interval}$. Doing so can further reduce power consumption. Activation could also depend on the sensor data. For example, only activate the transceiver if data meets certain thresholds, such a current rate of change, current high value, current low value, absolute difference from a previously exchanged value, percentage difference from a previously exchanged value, and the like. In some embodiments, instead of skipping certain fixed update intervals, the length of each interval can be made vary based on sensor data. For example, if the sensor data indicates a low glucose value and/or a hypoglycemic reaction is detected, the update interval value can be shortened from a normal update interval value so that more frequent readings are taken and transmitted.

In some embodiments, the update interval $T_{interval}$, the active period $T_{Active}$ and a frequency $F_{Activation}$ by which the transceiver is activated (e.g., every second, third or fourth update interval) may be variable. In certain embodiments, the above-identified parameters can be user configurable (e.g., by inputting a value for the variable using user interface of display device 110, 120, 130, 140) and/or automatically varied by the analyte sensor system 8 or display device 110, 120, 130, 140 based on one or more criteria. The criteria can include: (i) a monitored battery power of the sensor system 8, (ii) a currently measured, previously measured and/or predicted glucose concentrations meeting or exceeding a predetermined threshold, (iii) a glucose concentration trend of the host based on currently measured, previously measured and/or predicted glucose concentrations, (iv) a rate of change of glucose concentration of the host based currently measured, previously measured and/or predicted glucose concentrations meeting or exceeding a predetermined threshold, (v) whether the host is determined to be in or near hyperglycemia based on currently measured, previously measured and/or predicted glucose concentrations, (vi) whether the host is determined to be in or near hypoglycemia based on currently measured, previously measured and/or predicted glucose concentrations, (vii) user inputted activity of the host (e.g., exercising or sleeping), (viii) time since a sensor session has started (e.g., when a new sensor 10 is used), (ix) one or more errors detected by sensor system 8 or display device 110, 120, 130, 140, and (x) type of display device.

$T_{interval}$, $T_{Active}$, $F_{Activation}$ and/or other configuration items described herein may form part of a communication protocol profile that may be stored on any device that implements the fundamental communication protocol to allow for a customized use of the protocol for communicating analyte measurement values in the analyte sensor system 10 and display device 110, 120, 130, 140.

Facilitating Initial Data Connection Process

When a user wishes to pair a display device 110, 120, 130, 140 with a new analyte sensor system 8, he enters identification information (e.g. a serial number or some other unique identifier) associated with the analyte sensor system 8 (or the transceiver 316 of the system 8) in the display device, e.g., via a user interface (e.g., touchscreen) of the display device. For example, depending on the programmed update interval $T_{interval}$ and/or any sensor system initialization time, it can take 5 to 10 minutes before the transceiver 316 begins transmitting advertisement signals. It can therefore take up to 10 minutes to pair the analyte sensor system 8 with the display device 110, 120, 130, 140. In some embodiments the display device can be a mobile device such as a mobile phone 120, a tablet 130 or a smart watch 140 based on a particular mobile operating system (e.g., Android or iOS). A custom application running in the mobile device for handling an authentication procedure with the analyte sensor system 8 may be in an inactive or background mode so that the mobile device may not be able to complete the authentication procedure when the transceiver 316 begins to transmit advertisement signals. This problem can further increase the pairing time.

Figure 5:
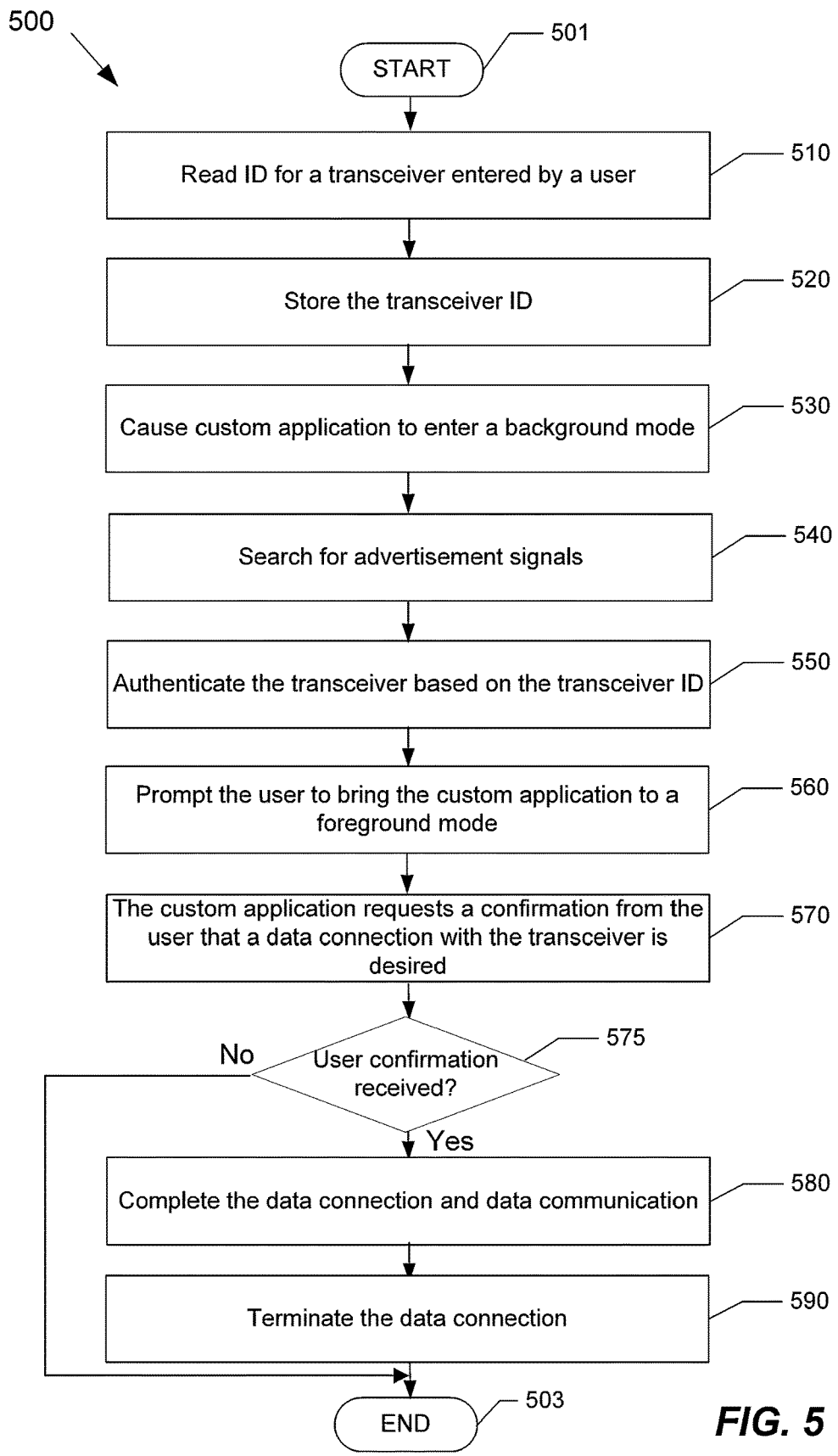
FIG. 5 is a flowchart illustrating an exemplary process for facilitating an initial setup procedure between an analyte sensor system and a mobile device according to certain aspects of the present disclosure.

One solution to the aforementioned problem is to cause the mobile device to display a message to the user via a user interface letting him know that the analyte sensor system 8 is ready for a data connection with the mobile device so that he can bring the custom application into a foreground mode. Once in the foreground mode, the custom application can optionally ask the user for confirmation that a data connection with the transceiver is desired. FIG. 5 is a flowchart illustrating an exemplary process 500 for facilitating an initial setup procedure between an analyte sensor system 8 and a mobile device 120, 130, 140 according certain aspects of the present disclosure. The various tasks performed in connection with the process 500 illustrated in FIG. 5 may be performed by a processor executing instructions embodied in non-transitory computer-readable medium. For example, the tasks performed in connection with the process 500 may be performed by hardware, software, firmware, or any combination thereof incorporated into one or more of computing devices, such as one or more of sensor system 8 and display devices 110, 120, 130 and 140 of FIG. 1 and/or FIG. 3. It should be appreciated that the procedure may include any number of additional or alternative tasks. The tasks shown in FIG. 5 need not be performed in the illustrated order, and the procedure may be incorporated into a more comprehensive procedure or process having additional functionality not described in detail herein.

As indicated above, the mobile device 120, 130, 140 can be based on a mobile operating system such as Android or iOS. The mobile device can be also configured to run a custom application for handling communication and management of analyte data from the analyte sensor system 8. In certain embodiments, the wireless data communication is based on a short-distance and/or low-power wireless communication protocol such as WiFi, Bluetooth and Bluetooth low energy (BLE). In certain embodiments, the mobile device is an iOS-based iPhone and the wireless communication protocol is the BLE.

The process 500 begins at a start state 501 and proceeds to operation 510 where the mobile device 120, 130, 140 reads identification information associated with the transceiver 316 of the analyte sensor system 8 that the user wishes to pair with. The identification information can be a serial number associated with the sensor system, for example. The user may enter this information via the custom application using a user interface such as a touchscreen display 122, 132, 142 provided in the mobile device 120, 130, 140. The process 500 proceeds to operation 520 where the user-entered identification information is stored in a memory 334 of the mobile device 120, 130, 140. The process 500 proceeds to operation 530 where the processor 330 of the mobile device 120, 130, 140 causes the custom application to enter a background mode. The custom application can be made to enter a background mode for a variety of reasons. For example, in certain embodiments, the background mode is entered after a predetermined time of inactivity. Depending on the mobile operating system, the predetermined time of inactivity can be between 10 and 100 seconds. In some embodiments, the background mode is entered after detecting conditions such as the memory usage of the mobile device exceeding some predetermined threshold and the mobile operating system and/or the user decides to place one or more active applications into a background mode.

The process 500 then proceeds to operation 540 where the mobile device 120, 130, 140 searches for advertisement signals from the transceiver 316 until the mobile device receives an advertisement signal. The process 500 proceeds to operation 550 where the mobile device, authenticates the transceiver 316 based on the user-entered identification information and a challenge value. As discussed above with respect to FIG. 4, the authentication operation 500 can include the mobile device requesting a challenge value from the transceiver 316; receiving the challenge value; generating or calculating a hash value from the challenge value and the identification information; transmitting the hash value to the transceiver; and receiving a confirmation indicating a successful authentication from the transceiver 316.

The process 500 then proceeds to operation 560 where the mobile device 120, 130, 140 prompts (e.g. via one or a combination of any of an audible alarm, vibratory alarm and pop up message) the user to bring the custom application into a foreground mode, e.g., by touching an icon associated with the custom application and/or the mobile device causes a pop-up message to appear on the display prompting the user to touch a selectable field corresponding to a custom application. Once the custom application is brought into a foreground mode, the process 500 proceeds to operation 570 where the custom application requests a confirmation from the user that a data connection with the transceiver 316 is desired. The process 500 proceeds to a query state 575 where it is determined whether such a confirmation is received from the user within a predetermined time. If the confirmation is received (Yes), the process 500 proceeds to operation 580 where the data connection with the transceiver 316 is completed, e.g., by sending a signal indicating the confirmation to the transceiver followed by a data communication in which the mobile device requests and receives an analyte value from the transceiver 316. After the data connection and data communication are completed, the process 500 proceeds to operation 590 where the data connection is terminated and then ends at an end state 503. On the other hand, if no confirmation is received from the user within a predetermined time (No), the process 500 ends without completing the pairing between the analyte sensor system 8 and the mobile device 120, 130, 140.

By way of example, the process 500 described above can be implemented in an Apple iPhone with iOS7 operating system. The iOS7 has "Restore/Restoration function" that reminds iOS7 that a custom application which has been suspended or placed in a background mode is expecting another Bluetooth event. Prior to this event, iOS7 can wake up the application and thereby cause it scan for Bluetooth signals (e.g., advertisements) from the transceiver 316.

Bringing a Custom Application Back from a Suspended State

In some cases, the processor 300 in the mobile device 120, 130, 140 may suspend the custom application if a certain condition occurs. For example, in some mobile operation systems, when it is determines that one or more applications are using an excessive amount of memory, the operating system may decide to deactivate or otherwise suspend one or more of the application(s) including a custom application in the mobile device that facilitates wireless communication with the analyte sensor system 8. When such a deactivation or suspension of the custom application occurs, the transceiver 338 in the mobile device may not scan or search for advertisement signals as often or at all, which in turn can hamper the ability of the mobile device to display updated analyte values and/or provide alerts based on the analyte values.

Figure 6:
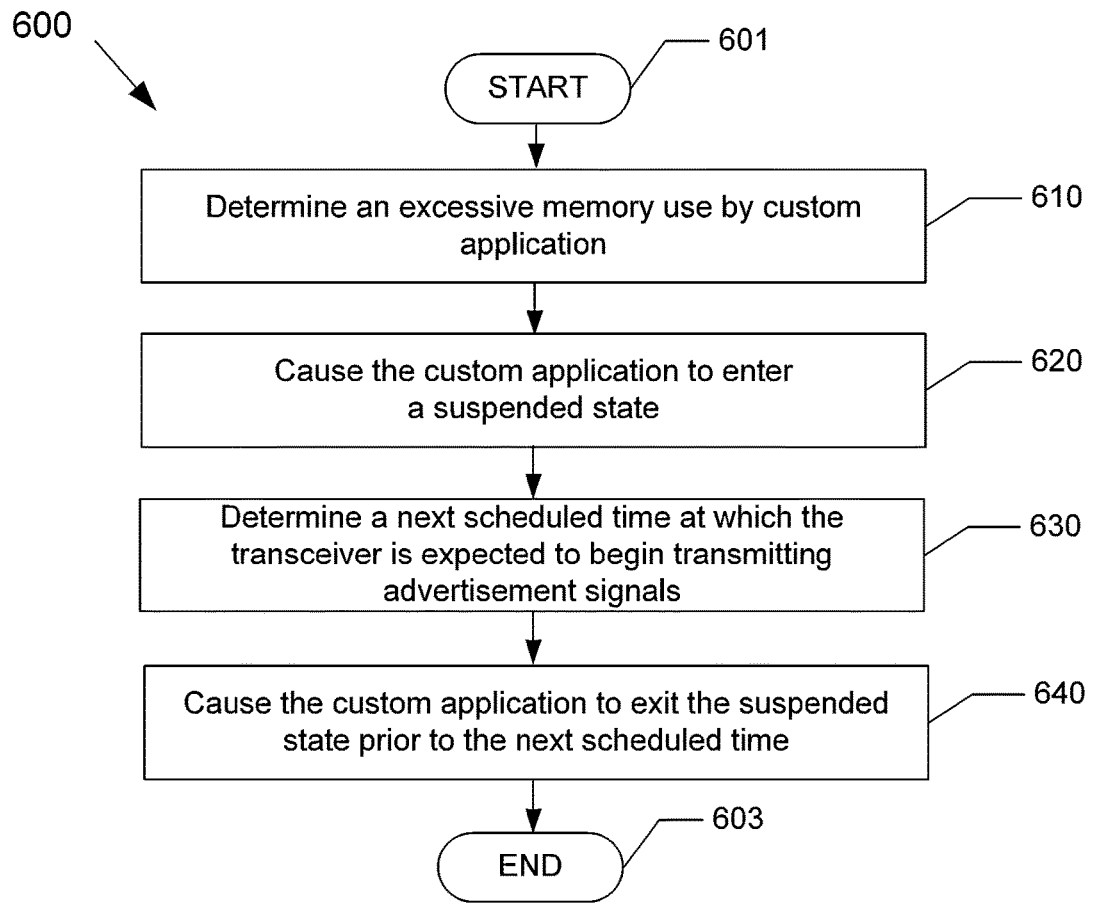
FIG. 6 is a flowchart illustrating an exemplary process for facilitating a wireless data communication between an analyte sensor system and a mobile device capable of wirelessly receiving analyte values from the analyte sensor system by causing a custom application to exit a suspended state prior to a next scheduled data communication event according certain aspects of the present disclosure.

This problem can be solved by use of a reminder feature available in some mobile operating systems such as Apple, Inc.'s iOS7 mobile operating system that reminds the operating system a custom application has been suspended and that the application is expecting a wireless communication event. In response to the reminder, the operating system can bring the custom application out of an inactive state (e.g., suspended, closed, in background, etc.) or just know to activate the BLE radio, thereby allowing the custom application to get ready for the upcoming wireless communication event. FIG. 6 is a flowchart illustrating an exemplary process 600 for facilitating a wireless data communication between an analyte sensor system 8 and a mobile display device 120, 130, 140 capable of wirelessly receiving analyte values from the analyte sensor system 8 by causing the custom application to exit an inactive state prior to a next scheduled data communication event according certain aspects of the present disclosure.

The process 600 begins at a start state 601 and proceeds to operation 610 where an excessive memory use by the custom application has been determined. An excessive memory use may be caused, for example, when memory usage on the mobile display device 110, 120, 130, 140 exceeds a certain preset storage threshold. An example can be a plurality of applications running on the mobile display device are using more memory than desired, which can result in poor performance overall. The process 600 proceeds to operation 610 where the processor 330 of the mobile display device 110, 120, 130, 140 causes the custom application to enter an inactive state in order to reduce overall memory usage, for example. As described above, when the custom application is placed in an inactive state, the transceiver 338 in the mobile device may be configured to not scan or search for advertisement signals as often or at all. The process 600 then proceeds to operation 620 where the processor 330 determines a next scheduled time at which the transceiver 316 is expected to begin transmitting a next set of advertisement signals. The process 600 proceeds to operation 630 where the processor 330 causes the custom application to exit the in active state prior to the next scheduled time. By bringing back the custom application from the suspended state before the transceiver 316 exits an inactive mode and begins transmitting a next set of advertisement signals, the mobile device is able to receive an advertisement signal and engage in data connection and communication with the transceiver 316. The process 600 ends at an end state 603 and then proceeds to requesting a connection and exchanging data as described above with respect to the operation 420 of FIG. 4.

Minimizing the Number of Advertisement Signals to Establish a Data Connection

As described above with respect to FIG. 4, once the transceiver 316 begins transmitting a set of advertisement signals 412, 422, it may take several advertisement signals for the display device 110, 120, 130, 140 to receive an advertisement signal and make a data connection with the transceiver 316. In some cases, the number can be as high as 10 or more. Transmission of such a high number of advertisement signals can drain a lot of power from the battery of the analyte sensor system 8. Thus, minimizing the number of advertisement signals that the transceiver 316 transmits can prolong the life of the analyte sensor system 8. In certain aspects of the present disclosure, this minimization can be achieved by causing the transceiver or radio unit 338 of the display device 110, 120, 130, 140 to exit an inactive mode and actively scan for advertisement signals from the transceiver 316 of the analyte sensor system 8 prior to the transmission of the advertisement signals. The particular time at which the transceiver 338 to exit the inactive mode can be calculated based on a connection interval received from the analyte sensor system 8 from a previous wireless communication cycle. The connection interval is indicative of an amount of time elapsed between the beginning of transmission of a series of advertisement signals by the transceiver 316 of the analyte sensor system 8 and a reception of a data connection request from the display device 110, 120, 130, 140 by the transceiver 316 in the previous wireless communication cycle. This scheme prevents the transceiver 338 of the display device 110, 120, 130, 140 from waking up too late and missing one or more advertisement signals at the beginning of the transmission.

Figure 7:
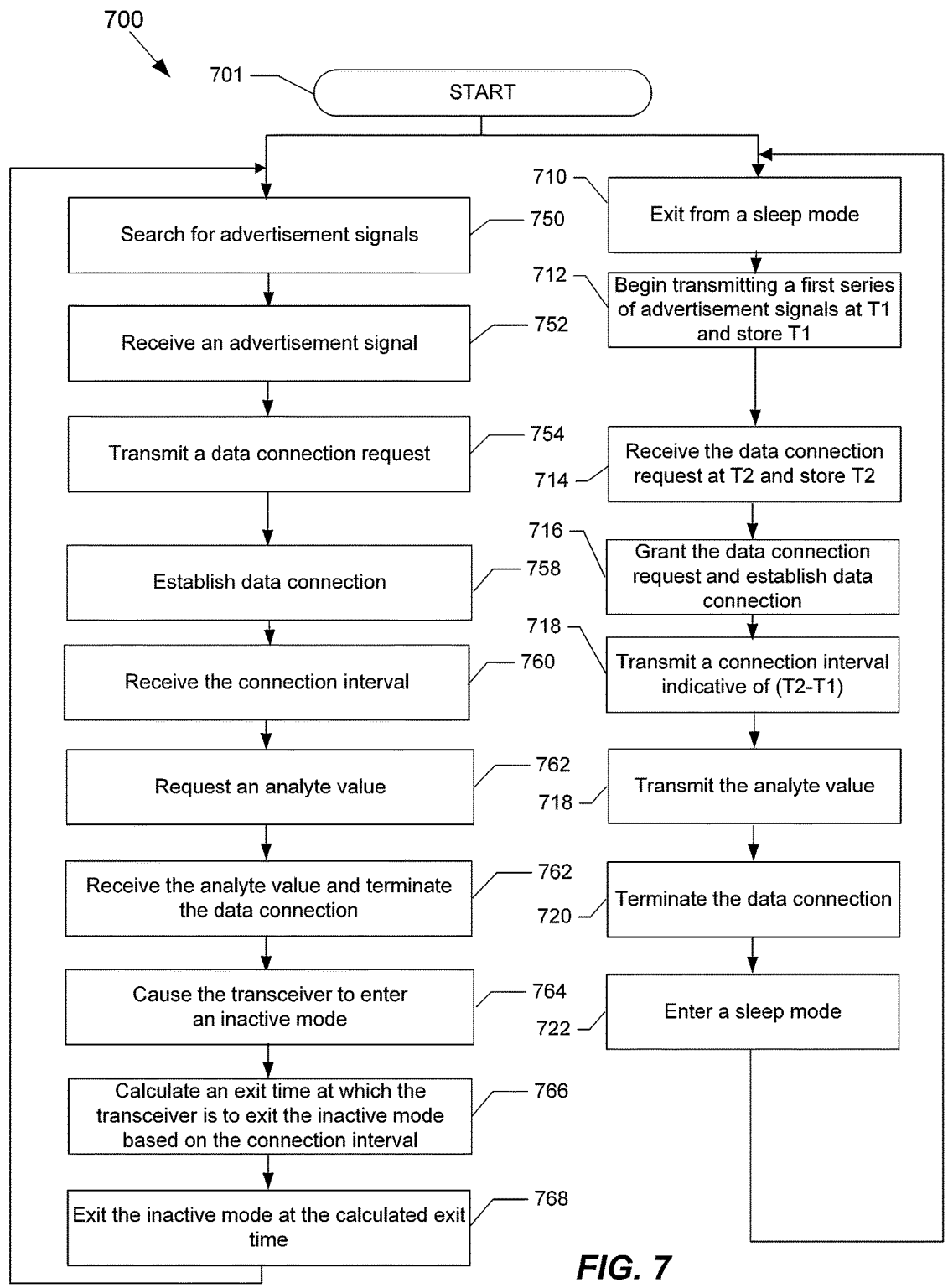
FIG. 7 is a flowchart illustrating an exemplary process for minimizing the number of advertisement signals that the transceiver of the analyte sensor system transmits before establishing a data connection with the display device according certain aspects of the present disclosure.

FIG. 7 is a flowchart illustrating an exemplary process 700 for minimizing the number of advertisement signals that the transceiver 316 of the analyte sensor system 8 transmits before establishing a data connection with the display device 110, 120, 130, 140 according certain aspects of the present disclosure. The flowchart shows two sets of operations. The set shown on the left-hand side with numerals ranging from 750 to 768 correspond to the operations performed at the display device 110, 120, 130, 140; and the set shown on the right-hand side with numerals ranging from 710 to 722 correspond to the operations performed at the analyte sensor system 8. The various tasks performed in connection with the process 700 illustrated in FIG. 7 may be performed by a processor executing instructions embodied in non-transitory computer-readable medium. For example, the tasks performed in connection with the process 700 may be performed by hardware, software, firmware, or any combination thereof incorporated into one or more of computing devices, such as one or more of sensor system 8 and display devices 110, 120, 130 and 140 of FIG. 1 and/or FIG. 3. It should be appreciated that the procedure may include any number of additional or alternative tasks. The tasks shown in FIG. 7 need not be performed in the illustrated order, and the procedure may be incorporated into a more comprehensive procedure or process having additional functionality not described in detail herein.

The process 700 begins at a start state 701 and proceeds to operation 710 where, at the analyte sensor system 8, the transceiver 316 exits from a sleep or inactive mode during which the transceiver 316 does not engage in a data communication with the display device 110, 120, 130, 140.

At the display device 110, 120, 130, 140, the process 700 proceeds to operation 750 where the processor 330 of the display device causes the transceiver 338 to search for advertisement signals from the analyte sensor system 8. At the analyte sensor system 8, the process 700 proceeds to operation 712 where the processor 314 of the analyte sensor system 8 causes the transceiver 316 to begin transmitting a first series of advertisement signals at a first time T1. The processor 314 of the analyte sensor system 8 measures the first time T1 using the real time clock (RTC) 320 and stores T1 in the memory 318.

At the display device 110, 120, 130, 140, the process 700 proceeds to operation 752 where the processor 330 of the display device receives an advertisement signal from the analyte sensor system 8 via the transceiver 338. Subsequently at operation 754, the processor 330 causes the transceiver 338 to transmit a data connection request to the analyte sensor system 8. At the analyte sensor system 8, the process 700 proceeds to operation 714 where the processor 314 receives the data connection request from the display device via the transceiver 316 at a second time T2. The processor 314 measures the second time T2 using the RTC 320 and stores T2 in the memory 318. At operation 716, the processor 314 grants the data connection request by causing the transceiver 316 to transmit a signal indicating the grant of the data connection request to the display device 110, 120, 130, 140 and establishing a data connection with the display device. At the display device, the processor 330 of the display device receives the signal from the analyte sensor system 8 and causes the transceiver 338 to establish a data connection with the transceiver 316 at operation 758.

At the analyte sensor system 8, the process 700 proceeds to operation 718 where the processor 314 causes the transceiver 316 to transmit a connection interval to the display device 110, 120, 130, 140. The connection interval is for use by the display device to calculate an exit time at which the display device is to exit from an inactive mode and start to search for advertisement signals from the analyte sensor system 8. The connection interval is calculated based on the first and second times, T1 and T2, and is indicative of a difference between those two times. For example, in some embodiments, the connection interval is the difference, namely, (T2−T1). In other embodiments, the connection interval is a function of the difference such as the current time+(T2−T1).

At the display device 110, 120, 130, 140, the process 700 proceeds to operation 760 where the processor 330 receives the connection interval from the analyte sensor system 8. The processor 330 then transmits a request for an analyte value to the analyte sensor system 8 at operation 762. At the analyte sensor system 8, the processor 314 receives the request and transmits the analyte value to the display device at operation 718 and causes the transceiver 316 to terminate the data connection at operation 720 and enter a sleep mode at operation 722. In some embodiments, the transceiver 316 is completely powered down. In other embodiments, the transceiver 316 enters a low-power mode.

At the display device 110, 120, 130, 140, the processor 330 receives the analyte value and terminates the data connection with the analyte sensor system 8 at operation 762. The processor 330 also causes the transceiver 338 to enter an inactive mode at operation 764. During the inactive mode, the transceiver 338 of the display device does not engage in a wireless data communication with the transceiver 316 of the analyte sensor system 8. At operation 766, the processor 330 also calculates an exit time at which the transceiver 316 is to exit the inactive mode based on the connection interval received from the analyte sensor system 8. In certain embodiments, the calculated exit time is given by: current time+update interval ($T_{interval}$)–the connection interval–notification delay–safeguard. As used herein, the notification delay is a measure of time elapsed between when a connection is first established and when a synchronization notification is actually sent. The actual duration might vary depending upon devices used. The safeguard is a measure of time that display device transceiver 338 has to wake up, and start scanning, before the analyte sensor system transceiver 316 wakes up. In some embodiments, the connection interval is from about 90 to 300 milliseconds and the notification delay is from about 100 to 300 milliseconds and the safeguard is typically from about 300 to 700 milliseconds. At operation 768, the processor 330 causes the transceiver 338 to exit the inactive mode at the calculated exit time so that the transceiver 338 can start searching for a next series of advertisement signals from the transceiver 316 of the analyte sensor system 8.

As can be seen in FIG. 7, the process 700 subsequently repeats so that, for a given wireless communication session, the transceiver 338 of the display device 110, 120, 130, 140 can exit from the inactive mode at an exit time that is calculated based on a connection interval received from the analyte sensor system 8 during a previous wireless communication session. When implemented in a mobile device using an Android operating system, this scheme has been shown to reduce the number of advertisement signals that the transceiver 316 needs to transmit on the average from over 50 to about 3 to 4. Further, use of this scheme has realized a reduction in power consumption for advertising by up to about 68% for the connection process.

Switching Between Display Devices

In some cases, it may be desirable or necessary for a user to switch between two or more display devices. For example, the user may want to normally view the glucose reading on his mobile phone 120. However, when the mobile phone 120 battery level is low, he may want to switch to the custom monitoring device 110 to continue to view the glucose reading from there. After charging the mobile phone, the user may want to switch back to the mobile phone 120 for a better viewing experience. Therefore, a convenient and efficient way to switch between display devices is desirable.

In addition, it is also desirable to be able to efficiently reject data connection requests from one or more display devices that are not the user-selected display device. For example, in a situation where the user selected the mobile phone 120 to be the only allowed display device, but the transceiver 316 may receive data connection requests from other display devices. In such cases, it is desirable to promptly reject the data connection request without spending a lot of time and battery power.

One solution for facilitating a switch between two display devices is to identify the single allowed display device (the mobile phone 120 in the example above) in a list and if a data connection request is received from a display device that is not the single allowed display device identified in the list, reject the request at a radio hardware level rather than at an upper software level. Such a list is can be implemented in a memory associated a processor controlling functions of the transceiver 316 at a radio hardware level. Such a processor may be part of the main processor 314 or part of the transceiver 316. In some embodiments, the processor is a link layer (LL) controller in the Bluetooth low energy (BLE) architecture. When a data connection request is received from a device, the radio hardware level controller determines whether the requesting device is identified in the list and, if it is not identified in the list, rejects the request at a radio hardware level rather than at an upper software level. This can significantly reduce the time and battery power associated with rejecting data connection requests from unwanted devices. In some embodiments, there can be more than one allowed display device. That is, there can be multiple display devices that are connected to and communicating with the analyte sensor system 8 at the same time.

In certain embodiments, the analyte sensor system 8 can also store information identifying one or more display devices that have been previously paired with the transceiver. In some embodiments, such information is stored in the same list or memory where the information identifying the single allowed display device is stored. In other embodiments, such information is stored in a different list or memory. By storing this information, the devices can form an authenticated communication more quickly and efficiently.

Figure 8A:
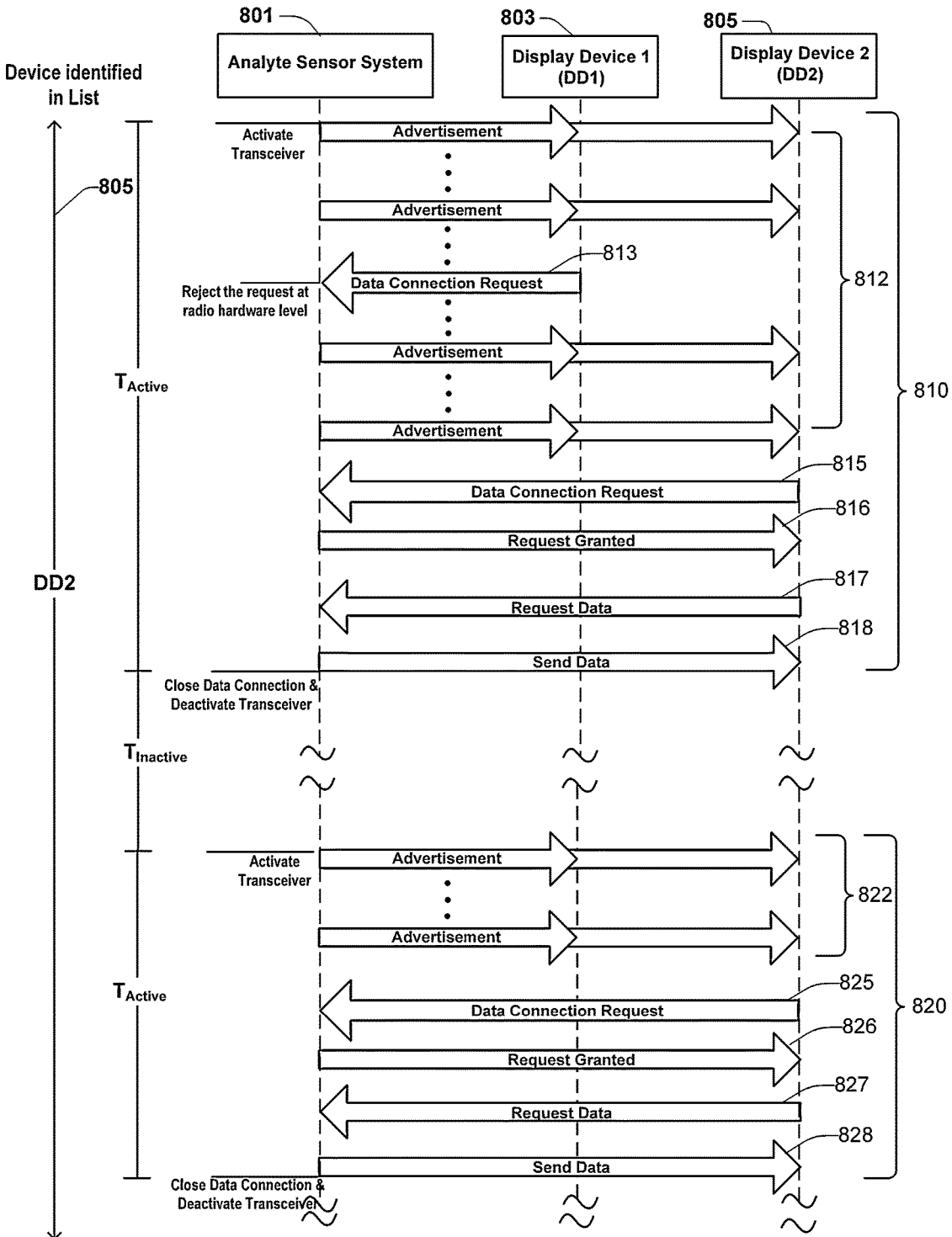
FIGS. 8A and 8B represent a flow diagram illustrating an exemplary system and method for rejecting a data connection request from a display device not identified in a list containing a single allowed display device according to certain aspects of the present disclosure.
Figure 8B:
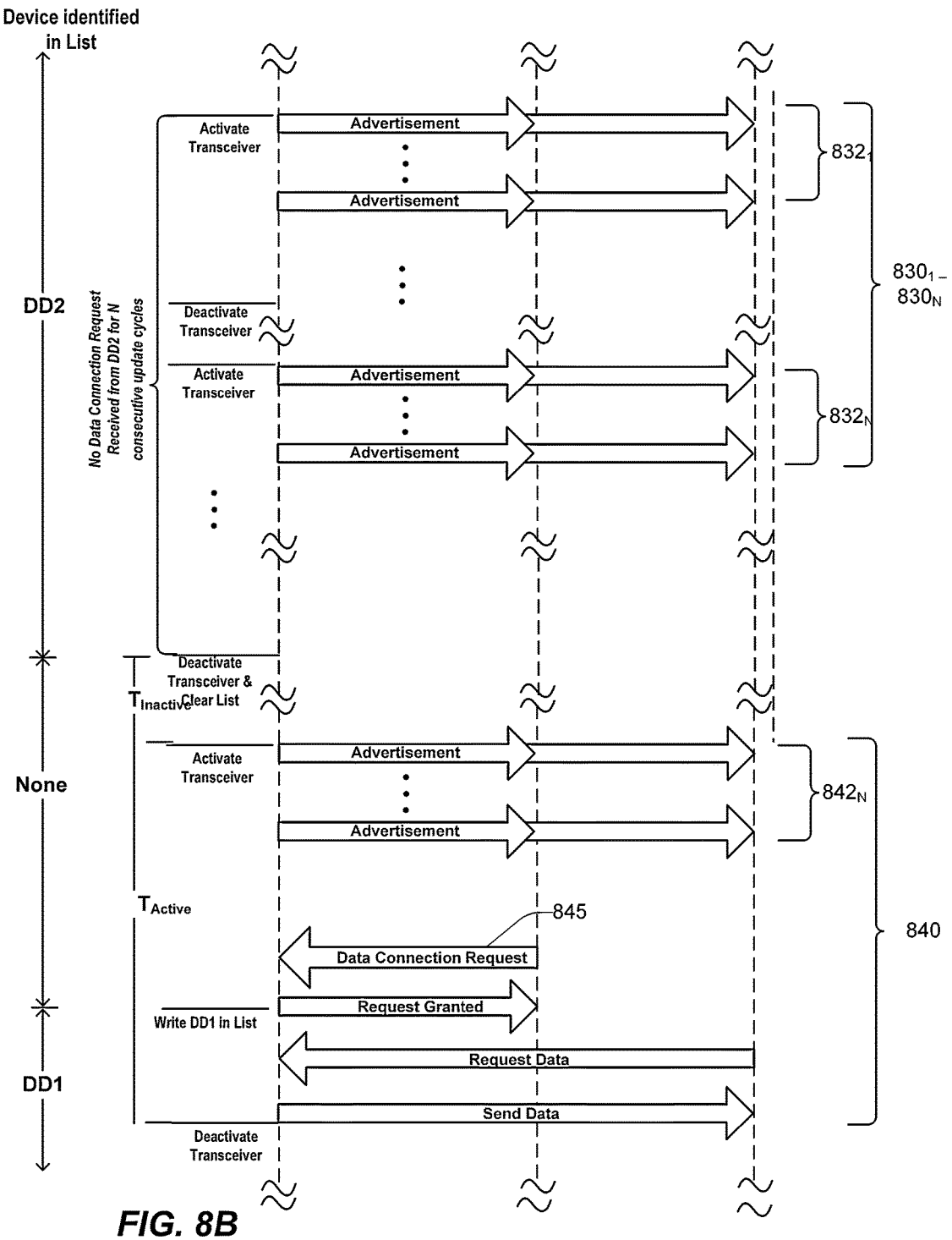

FIGS. 8A and 8B represent a flow diagram illustrating an exemplary system and method for rejecting a data connection request from a display device not identified in a list containing a single allowed display device according to certain aspects of the present disclosure. In some embodiments, however, there can be multiple allowed display devices in the list. FIG. 8A shows an analyte sensor system 801, a first display device (DD1) 803 and a second display device (DD2) 805. A vertical arrow 805 with the designation "Device Identified in List" on the left side of FIG. 8 identifies the display device currently stored in the list containing a single allowed list. In the illustrated example, DD2 805 is the display device identified in the list in FIG. 8A. In FIG. 8B, the content of the list changes from DD2 805 to none to DD1 803.

For ease of illustration only without any intent to limit the scope of the disclosure in any way, the analyte sensor system 801 of FIGS. 8A and 8B is described with reference to the analyte sensor system 8 depicted in FIG. 4. Similarly, the first and second display devices 8031, 805 are described with reference to the display device 110, 120, 130, 140 depicted in FIG. 4.

Connect to FIG. 4 to explain that DD1 and DD2 have been already authenticated and paired. At the beginning of a first communication session 810, the analyte sensor system 801 begins to transmit a first series of advertisement signals 812. At this stage, both DD1 803 and DD2 805 have been paired with the analyte sensor system 8 in accordance with paring operations 414 and 416 described above with respect to FIG. 4. However, only DD2 805 is currently on the list containing a single allowed display device. The advertisement signals 812 can be received by both DD1 803 and DD2 805, the DD2 805 being the display device identified in the list for containing a single allowed display device. In the illustrated example, the DD1 803 receives an advertisement signal from the analyte sensor system 8 and responds first by transmitting a first data connection request 813. The DD2 805 may have also received the advertisement signal but could not respond to the signal before the DD1 803 did. So, a response signal from the DD2 805 is not received or recognized by the transceiver 316 of the analyte sensor system 8. By comparing the ID of the DD1 803 included in the first data connection request 813 to the identification information stored in the list for containing a single allowed display device, a processor (e.g., a link layer (LL) controller) controlling functions of a radio hardware level of the transceiver 316 determines the DD1 803 is not the display device identified in the list and rejects the first connection request 813 at a radio hardware level. In certain embodiments, the analyte sensor system 8 transmits a signal causing the DD1 803 to stop sending additional connection requests. In other embodiments, the DD1 803 stops sending additional connection requests if it does not receive a response to the first advertisement signal within a predetermined time.

In the illustrated example, after rejecting the first data connection request 813 from the DD1 802, the transceiver 316 of the analyte sensor system 801 continues to transmit additional advertisement signals during the first wireless communication session 810 as shown in FIG. 8A. In response to one of the additional advertisement signals, the DD2 805 transmits a second data connection request 815. The processor determines that the DD2 805 is the display device identified in the list for containing a single allowed device and grants the request. Upon completion of the data connection, the DD2 805 transmits a request for data 817 (e.g., analyte data) from the analyte sensor system 801 and the analyte sensor system 801 transmits the requested data 818 to the DD2 805. After completion of the data communication process 817, 818, the data connection between the analyte sensor system 801 and the DD2 805 is terminated/closed and the transceiver 316 of the analyte sensor system 801 is deactivated by causing it to enter a sleep mode.

After a period of inactivity, indicated by the inactive time $T_{Inactive}$ (during which an analyte measurement can be made by the analyte sensor 312 as described above with respect to FIG. 4), a second communication session 820 begins with the transceiver 316 of the analyte sensor system 801 beginning to transmit a second series of advertisement signals 822. This time, the DD2 805 receives an advertisement signal and responds first by transmitting a second data connection request 815. By comparing the ID of the DD2 805 included in the second data connection request 815 to the identification information stored in the list for containing a single allowed display device, the processor of the analyte sensor system 810 determines that the DD2 805 is the currently allowed display device and grants the request, e.g., by transmitting a signal 826 indicative of the grant. Upon completion of the data connection, the DD2 805 transmits a request for data 827 and the analyte sensor system 801 transmits the requested data 828. After completion of the data communication process 827, 828, the data connection between the analyte sensor system 801 and DD2 805 is terminated/closed and the transceiver 316 of the analyte sensor system 801 is deactivated by causing it to enter a sleep/powered-down mode.

If a certain predetermined condition is met, the list for containing a single allowed display device may be cleared so that another display device can connect to the analyte sensor system 8 without being rejected at the radio hardware level. This feature solves the problem of trying to connect with a new display device when the current display device on the list is lost or not working. FIG. 8B illustrates one exemplary process by which the list can be cleared when no data connection request is received from the display device identified in the list within a predetermined number (N) of wireless communication sessions $830_1$-$830_N$. As can be seen in FIG. 8B, N sets of advertisement signals $832_1$-$832_N$ are transmitted and no data connection request is received from the DD2 805, the display device identified in the list for containing a single allowed display device. When this occurs, the processor controlling the radio functions of the transceiver 316 erases the information identifying the DD2 805 stored in the list.

In a subsequent communication session 840, the transceiver 316 transmits a set of advertisement signals 842 and, this time, a third data connection request 845 is received from the DD1 803. Note that, at this stage, the list for containing a single allowed display device is empty. Upon receiving the third data connection request 845, the processor controlling the radio functions of the transceiver 316 grants the request 845 and writes information identifying the DD1 803 in the list. As long as the DD1 803 is identified in the list, subsequent data connection requests received from the DD1 803 would be granted without being rejected at the radio hardware level.

Another predetermined condition that can cause the list to be cleared is reception of a signal from the listed display device (i.e., the display device identified in the list) that indicates that the listed display device to be cleared from the list. This can happen, for example, when the user who wants to switch to another display device (e.g., from a mobile phone 120 to a custom display device 120 or vice versa) explicitly enters a command on the currently listed display device to clear the listed display device from the list. Another possibility is that the listed device automatically transmits the clearance signal if it determines that the device is about to be turned off due to a low battery level, for example.

As described above, the analyte sensor system 8 is also configured to store information identifying one or more display devices that have been paired with the transceiver either in the same list or in a different list. If such information is not stored in the analyte sensor system 8, meaning that no other display device has been paired with the transceiver, the transceiver continues to accept data connection requests from one or more display devices until at least one display device is paired with the transceiver and information identifying the paired display device is stored in a list for storing one or more previously paired display devices.

Figure 9A:
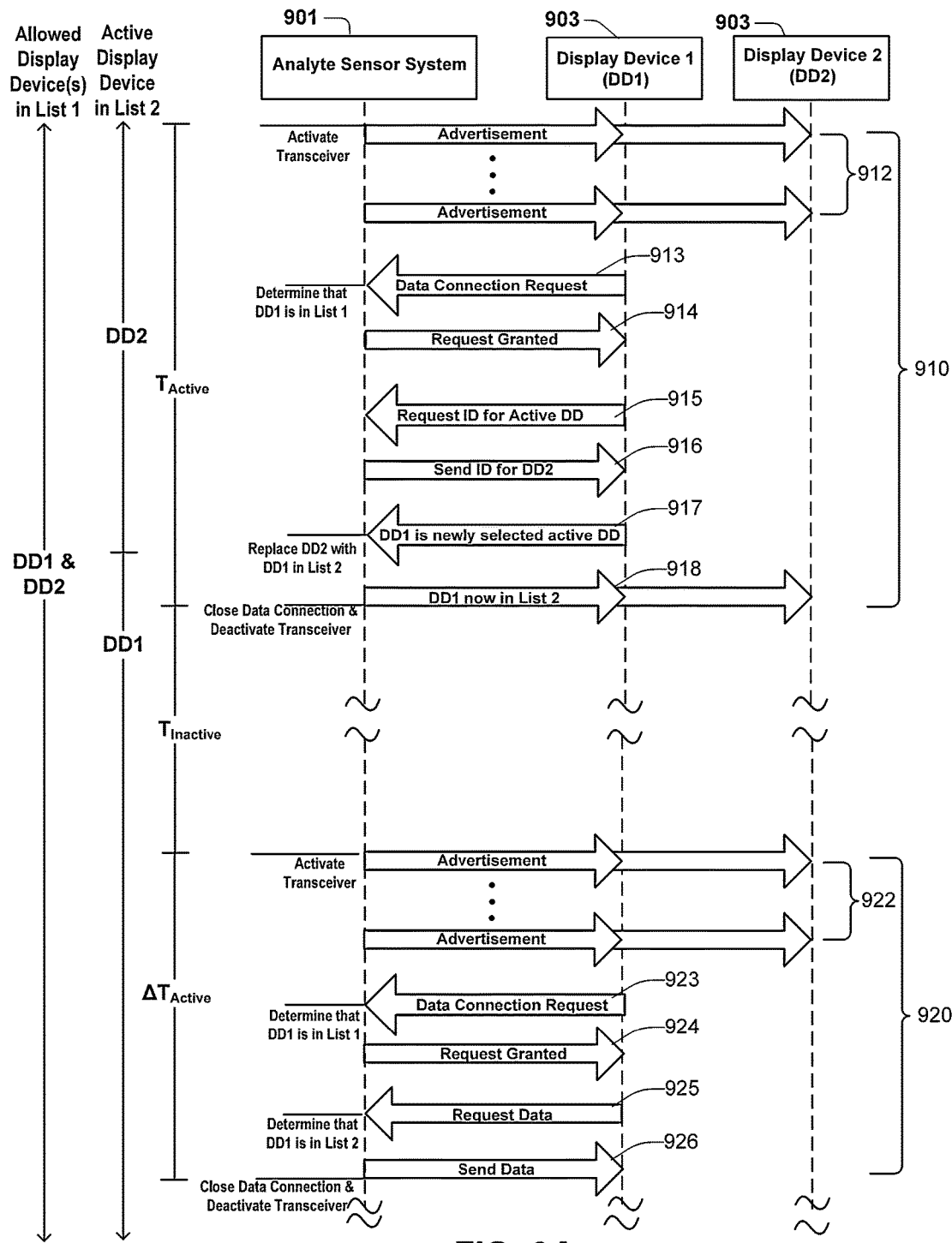
FIGS. 9A and 9B represent a flow diagram illustrating an exemplary procedure for facilitating a switch between two display devices that makes use of two separate lists according certain aspects of the present disclosure.
Figure 9B:
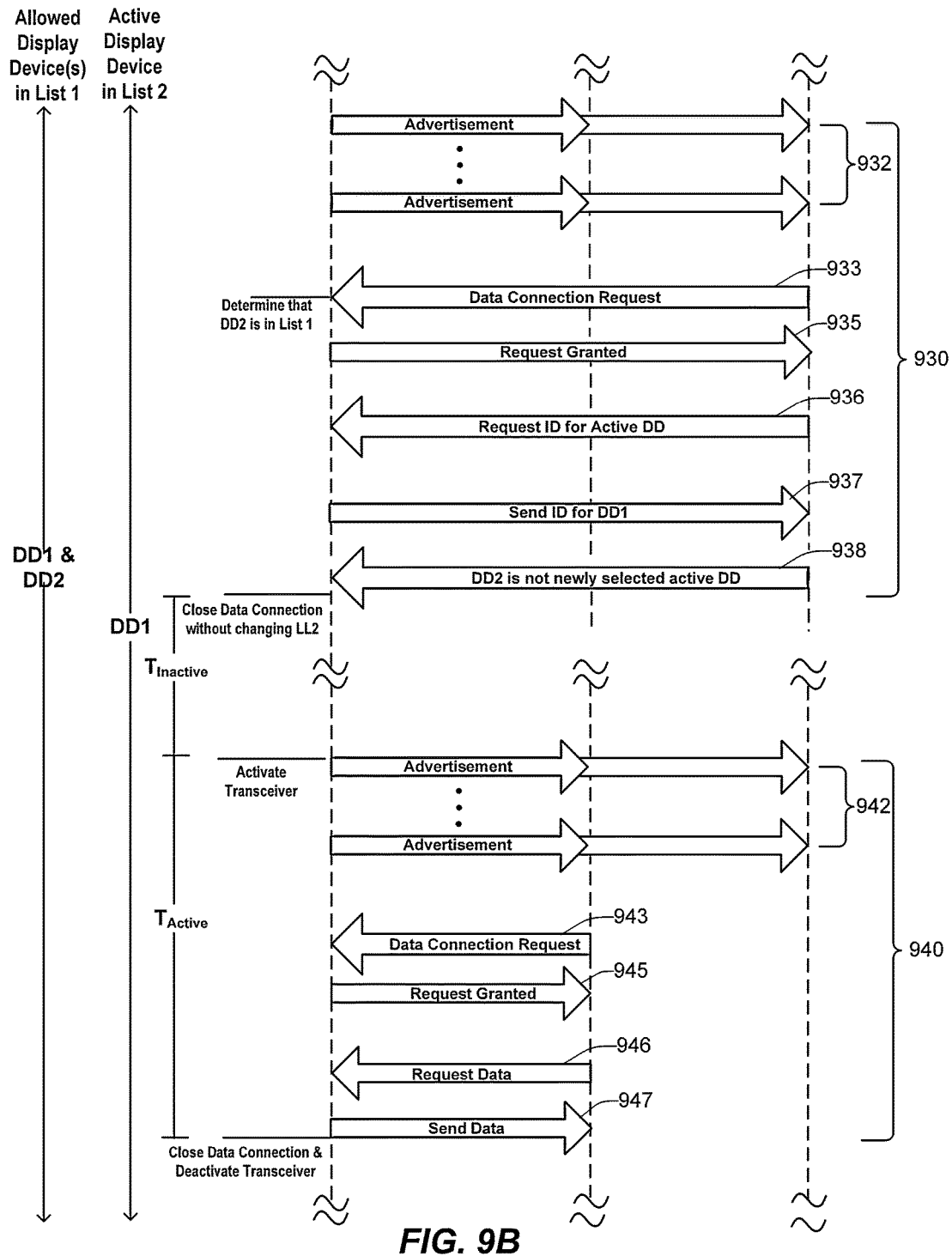

FIGS. 9A and 9B represent a flow diagram illustrating an exemplary procedure for facilitating a switch between two display devices that makes use of two separate lists according certain aspects of the present disclosure. A first list is for containing information identifying one or more allowed display devices and a second list is for containing information identifying a single currently active display device, i.e., a display device that has been selected to receive and display analyte values from the analyte sensor system. The first list is preferably implemented in a memory associated the processor controlling functions of the transceiver at a radio hardware level described above. The second list can be implemented in the same memory comprising the first list or in a different memory.

For ease of illustration only without any intent to limit the scope of the disclosure in any way, the analyte sensor system 901 of FIGS. 9A and 9B is described with reference to the analyte sensor system 8 depicted in FIG. 4. Similarly, the first and second display devices 903, 905 are described with reference to the display device 110, 120, 130, 140 depicted in FIG. 4.

At this stage, both DD1 903 and DD2 905 have been paired with the analyte sensor system 901 in accordance with paring operations 414 and 416 described above with respect to FIG. 4 and are on the list containing allowed display devices. However, only DD2 905 is currently on the list containing a single active display device. In the illustrated example, it is assumed that the user has decided to select the DD1 903 as the new active display device to receive and display analyte values from the analyte sensor system 901. At the beginning of a first communication session 910 shown in FIG. 9A, the transceiver 316 of the analyte sensor system 801 begins to transmit a first series of advertisement signals 912. The advertisement signals 812 can be received by both DD1 903 and DD2 905. As indicated by two vertical arrows in the left side of the figure, at this stage, both DD1 903 and DD2 905 are identified in the first list for containing information identifying one or more allowed display devices and only DD2 905 is identified in the second list for containing information identifying a single active display device. The DD1 903, the newly selected active display device, receives an advertisement signal from the analyte sensor system 901 and responds first by transmitting a data connection request 913 to the analyte sensor system 901. By comparing the ID of the DD1 903 included in the first data connection request 913 to the data stored in the first list for containing one or more allowed display devices, the processor (e.g., a link layer (LL) controller) controlling functions of the transceiver 316 at a radio hardware level determines that the DD1 903 is identified in the first list and grants the data connection request 914 by transmitting a signal 914 indicating the grant to the DD1 903.

The DD1 903 then transmits a request 915 for identification of the display device identified in the second list. The analyte sensor system 901 responds to the request 915 by transmitting a signal 916 indicating that the DD2 905 is identified in the second list. Upon receiving the signal 916, the DD1 903 transmits a signal 917 indicating that it has been selected as a new active display device. In response, the analyte sensor system 901 changes the second list to indicate that the DD1 903 is the currently active display device. In some embodiments, the analyte sensor system 901 also transmits a signal 918 indicating that the DD1 903 is now identified in the second list. From the signal 919, the DD2 905 can be notified that the display device 905 is no longer the active display device and can cause the display device 905 to stop responding to advertisement signals during a next communication session and/or to enter an inactive state. After transmission of the signal 917 (and possibly also the signal 918), the data connection is terminated and the transceiver 316 is deactivated, thereby completing the first wireless communication session 910.

After a predetermined period of inactivity indicated by the inactive time $T_{Inactive}$ (during which one or more analyte measurements from the analyte sensor 312 can be taken), a second wireless communication session 920 begins with the transceiver 316 of the analyte sensor system 901 beginning to transmit a second series of advertisement signals 922. The DD1 903 receives an advertisement signal and responds first by transmitting a second data connection request 923. Upon receiving the second data connection request 923, the analyte sensor system 901 determines that the DD1 903 is identified in the first list and transmits a signal 924 indicating a grant of the second data connection request 923 to the DD1 903. The DD1 903 then transmits a request 925 for data and the analyte sensor system 901 responds to the request 925 by transmitting the requested data 926. After the data communication 925, 926, the data connection is terminated and the transceiver 316 is deactivated, thereby completing the second wireless communication session 920.

FIG. 9B illustrates what happens when a display device that is not the currently active display device sends a data connection request to the analyte sensor system 901 according to certain aspects of the present disclosure. In the illustrated example, in a third wireless communication session 930, the DD2 905 transmits a third data connection request 933 in response to a series of advertisement signals 932 transmitted from the analyte sensor system 901. In response to the third data connection request 933, the analyte sensor system 901 grants the third data connection request 933 after determining that the DD2 905 is identified in the first list and transmits a signal 924 indicating the grant to the DD2 905. The DD2 905 then transmits a request 936 for identification of the display device identified in the second list. The analyte sensor system 901 responds to the request 936 by transmitting a signal 937 that the DD1 902 is identified in the second list. Upon receiving the identification information 937, the DD2 905 transmits a signal 938 indicating that the display device 905 is not a newly selected active display device. In response, the analyte sensor system 901 terminates/closes the data connection and in some embodiments the transceiver 316 may be deactivated (i.e., caused to enter a sleep state) without changing the second list. Because the second list was not changed during the third communication session 930 and therefore still identifies the DD1 903 as the currently active display device, a data connection process 943 and 945 and data communication process 946, 947 occur normally during a fourth wireless communication session 940 shown in FIG. 9B.

Figure 10:
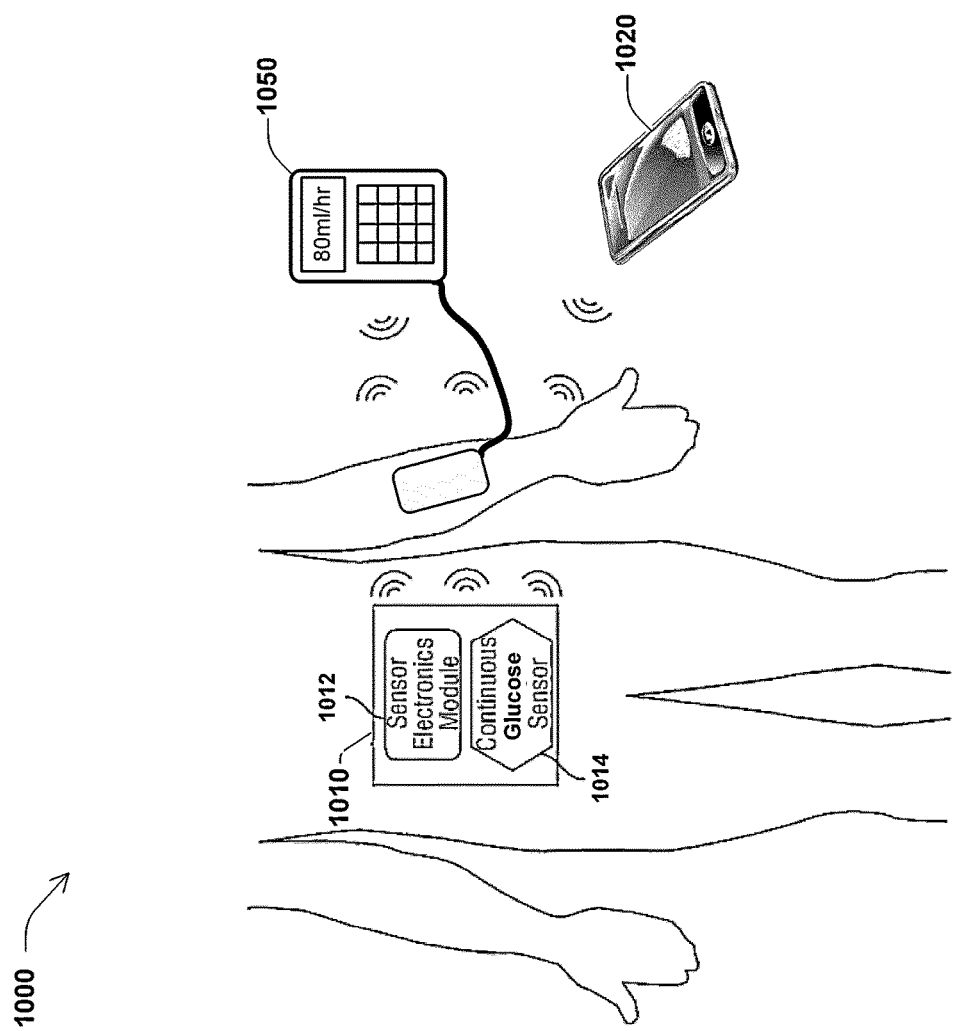
FIG. 10 is a diagram illustrating a wireless data communication system including an analyte sensor system, an active display device, and a passive display device according to certain aspects of the present disclosure.

In the system and method of FIGS. 9A and 9B, only one active display device is allowed to establish a data connection with the analyte sensor system 901 and receive sensor information such as analyte data from the sensor system 901. In general, more than one display devices can be allowed to establish data connections with the analyte sensor system 901. However, for the ease of illustration, only one active display device is allowed to establish a data connection in the example of FIGS. 9A and 9B. In some embodiments, the list containing one or more allowed display devices and/or the list containing one or more active display devices can be erased if no connection request(s) are received from the display devices on the list(s) for a predetermined number of wireless communication sessions. In some cases, it is desirable to allow a passive device to receive analyte data and/or other information from the analyte sensor system without being paired and/or connected to the analyte sensor system. FIG. 10 is a diagram illustrating a wireless data communication system 1000 including an analyte sensor system 1010, an active display device 1020, and a passive device 1050 according to certain aspects of the present disclosure. In the illustrated example, the analyte sensor system 1010 is a continuous glucose sensor system comprising a sensor electronics module 1012 and a continuous glucose sensor 1014; the active display device 1020 is a mobile phone; and the passive device 1050 is an insulin pump for administering insulin to the user. For a variety of reasons, it may be desirable for the insulin pump 1050 to receive and track glucose values transmitted from the continuous glucose sensor system 1010. One reason is to provide the insulin pump 1050 a capability to suspend insulation administration when the glucose value falls below a threshold value. One solution that allows a passive device (e.g., the insulin pump 1050) to receive desired data (e.g., glucose values) without needing to establish an authenticated communication channel with the analyte sensor system (e.g., the glucose sensor system 1010) is to include the desired data in the advertisement signals transmitted from the analyte sensor system. The data included in the advertisement signals can be encoded so that only a device that has the identification information associated with the analyte sensor system 1010 can decode the data. In some embodiments, the active display device 1020 extracts and uses the data included in the advertisement signals. In other embodiments, the active display device 1020 does not extract the data included in the advertisement signals and instead obtains the data after the display device 1020 establishes a data connection with the analyte sensor system 1010 in the manner described above with respect to FIG. 4.

Figure 11:
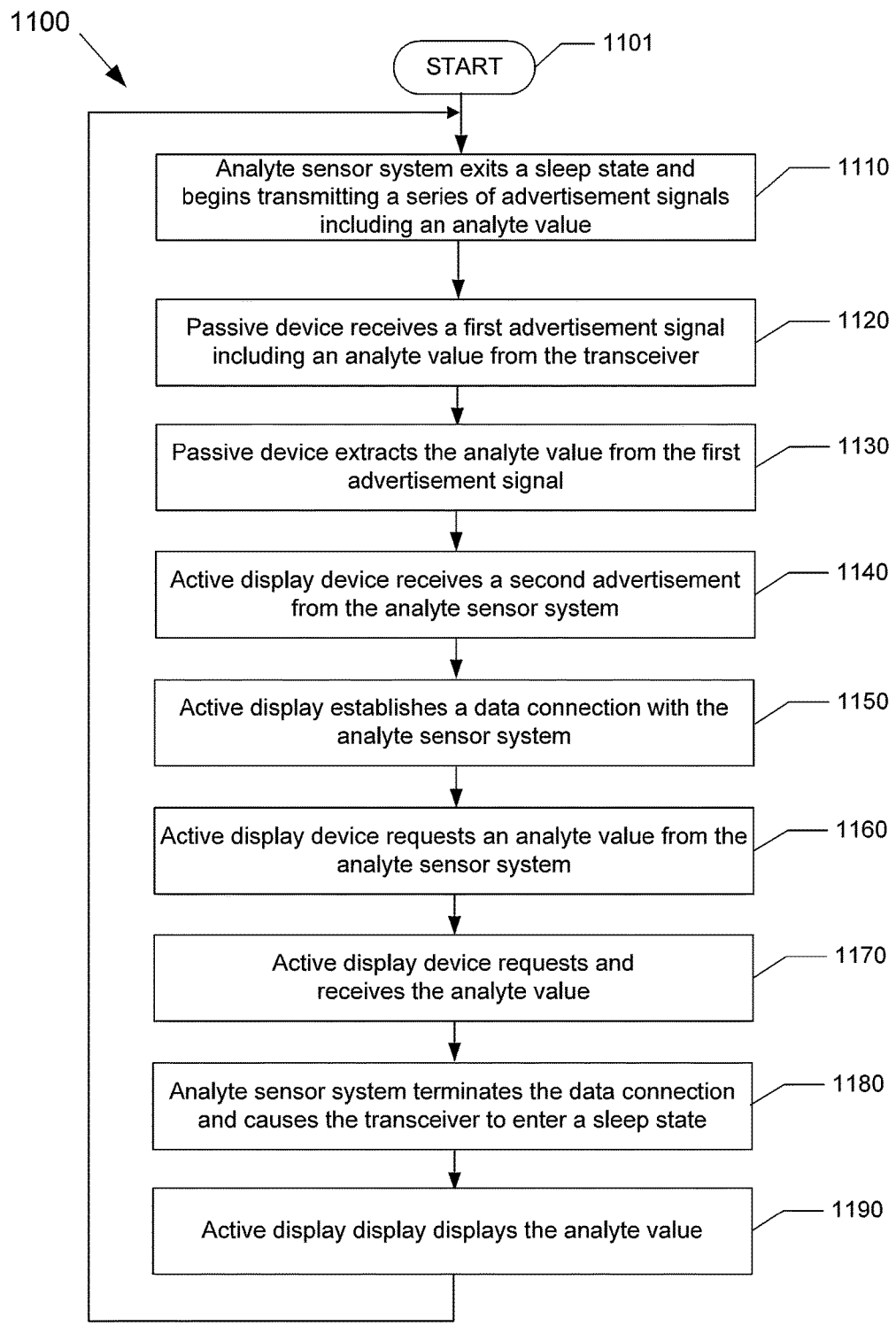
FIG. 11 is a flowchart illustrating an exemplary process for allowing a passive device to receive desired data from an analyte sensor system without being paired or connected to the analyte sensor system according to certain aspects of the present disclosure.

FIG. 11 is a flowchart illustrating an exemplary process 1100 for allowing a passive device to receive desired data from an analyte sensor system without being paired or connected to the analyte sensor system according to certain aspects of the present disclosure. The process 1100 begins at a start state 1101 and proceeds to operation 1110 where a transceiver of the analyte sensor system 1010 exits a sleep mode and begins to transmit a series of advertisement signals that include an analyte value (or other information to be used by the passive device). The process 1100 proceeds to operation 1120 where the passive device 1050 receives a first advertisement signal including the analyte value. In certain embodiments, the analyte value included in the advertisement signals is encoded so that the analyte value can be read or decoded only by having identification information associated with the analyte sensor system 1010. As an example, the user previously entered a serial number associated with the analyte sensor system 1010 into the passive display device. The process 1100 proceeds to operation 1130 where the passive device 1050 extracts the analyte value from the first advertisement signal. In those embodiments where the analyte value included in the advertisement signals is encoded, the extracting process involves decoding the encoded analyte value using a key or code that can be generated by the use of the identification information associated with the analyte sensor system 1010. The passive device 1050 can use the extracted analyte value for various purposes. For example, in those embodiments where the passive device 1050 is an insulin pump, the extracted glucose value can be displayed on an interface of the device 1050, used for calculating an optimal insulin administration rate, and/or to suspend the insulin administration when the glucose value falls below a threshold value.

The process 1100 proceeds to operation 1140 where the active display device 1020 receives an advertisement signal from the transceiver of the analyte sensor system 1010. This advertisement signal can be the same as the one received by the passive device or a different one. The process 1100 proceeds to operation 1150 where the active display device 1020 establishes a data connection with the transceiver using one or more data connection processes, examples of which are described above with respect to FIGS. 4, 5, 6, 7, 8A, 8B, 9A, 9B. The process 1100 proceeds to operation 1170 where the active display device 1020 requests and receives an analyte value or other information from the analyte sensor system 1010 using one or more data communication processes, example of which are described above with respect to FIGS. 4, 5, 6, 7, 8A, 8B, 9A, 9B. The process 1100 proceeds to operation 1180 where the analyte sensor system 1010 terminates the data connection with the active display device 1020 and causes the transceiver of the analyte sensor system 1010 to enter a sleep mode. The process 1100 repeats by looping back to the operation 1110.

The various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more non-transitory computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred', 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for a wireless data communication between an analyte sensor system and a plurality of display devices capable of displaying analyte values wirelessly received from the analyte sensor system, the method comprising:
    a processor of an analyte sensor system causing transmitting a first series of advertisement signals from a transceiver of the analyte sensor system;
    receiving at the transceiver of the analyte sensor system a first data connection request from a transceiver of a first display device;
    determining by the processor of the analyte sensor system that the first display device is identified in a first list containing one or more allowed display devices;
    establishing by the processor of analyte sensor system a first data connection between the transceiver of the analyte sensor system and the transceiver of the first display device;
    receiving a request from the transceiver of the first display device, wherein the request is for identifying the first display device in a second list, and wherein the second list stores information about a currently active display device configured to receive and display analyte values from the analyte sensor system;
    responsive to the request, transmitting from the analyte sensor system a first signal to the first display device indicating that the first display device is not identified, and a second display device that is different from the first display device is identified in the second list;

receiving at the analyte sensor system a second signal from the first display device indicating that the first display device is a newly selected active display device;

responsive to the second signal, changing by the processor of the analyte sensor system the second list, wherein the changing to the list includes indicating that the second display device is no longer the active display device, and selecting the first display device as the single currently active display device for receiving and displaying analyte values from the analyte sensor system; and terminating by the processor of the analyte sensor system the first data connection with the first display device.

2. The method of claim 1, further comprising transmitting a third signal from the analyte sensor system to the first display device indicating that the first display device is the new selected single currently active display device.

3. The method of claim 1, further comprising:
reading from the second list first data identifying the second display device as the currently active display device, wherein the changing comprises replacing the first data with second data identifying the first display device.

4. The method of claim 3, wherein the second signal comprises a request to write to the second list the second data identifying the first display device as the currently active display device.

5. The method of claim 1, further comprising:
transmitting a second series of advertisement signals;
receiving a second data connection request from the first display device;
establishing a second data connection with the first display device;
determining that the first display device is identified in the second list;
transmitting an analyte value to the first display device; and
terminating the second data connection with the first display device.

6. The method of claim 5, further comprising:
transmitting a third series of advertisement signals;
receiving a third data connection request from the second display device;
establishing a third data connection with the second display device if it is determined that the second display device is identified in the first list;
transmitting a fourth signal to the second display indicating that a different display device is identified in the second list;
receiving a fifth signal from the second display device, the fifth signal indicating that the second display device is not a newly selected active display device; and
terminating the third data connection with the second display device without changing the second list.

7. An analyte sensor system configured for a wireless data communication with a plurality of display devices capable of displaying analyte values from the analyte sensor module, the analyte sensor system comprising:
an analyte sensor;
a transceiver configured to transmit and receive wireless signals; and
a processor operatively coupled to the analyte sensor, and the transceiver and configured to:

cause the transceiver to transmit a first series of advertisement signals,
receive a first data connection request from a first display device,
determine that the first display device is identified in a first list containing one or more allowed display devices,
establish a first data connection with the first display device,
receive a request from the first display device, wherein the request is for identifying the first display device in a second list, and wherein the second list stores information about a currently active display device configured to receive and display analyte values from the analyte sensor system,
responsive to the request, read from the second list first data identifying a second display device as a currently active display device,
transmit the first data to the first display device,
in response to the transmission of the first data, receive a request to write to the second list second data selecting the first display device as a currently active display device for receiving and displaying analyte values from the analyte sensor system and indicating that the second display device is no longer the active display device,
write the second data to the second list, and
terminate the first data connection with the first display device.

8. The analyte sensor system of claim 7, wherein the analyte sensor is a continuous glucose sensor.

9. The analyte sensor system of claim 7, wherein the first display device and the second display device are selected from a group consisting of: a custom analyte monitoring device and a mobile device.

10. The analyte sensor system of claim 9, wherein the mobile device is a mobile phone.

11. The analyte sensor system of claim 7, wherein the processor is configured to reject a data connection request from a display device not identified in the first list at a radio hardware level.

12. The analyte sensor system of claim 11, wherein the processor comprises a link layer (LL) controller.

13. The analyte sensor system of claim 12, wherein the first list is a white list maintained in the LL controller.

14. The analyte sensor system of claim 7, wherein the processor is further configured to:
cause the transceiver to transmit a second series of advertisement signals,
receive a second data connection request from the first display device,
cause the transceiver to establish a second data connection with the first display device,
determine that the first display device is identified in the second list,
cause the transceiver to transmit an analyte value to the first display device, and
cause the transceiver to terminate the second data connection with the first display device.

15. The analyte sensor system of claim 14, wherein the processor is further configured to:
cause the transceiver to enter a sleep mode, and
cause the transceiver to exit the sleep mode after a predetermined time.

16. The analyte sensor system of claim 15, wherein the predetermined time is between about 200 and 300 seconds.

17. The analyte sensor system of claim 15, wherein the processor is further configured to take a measurement of an output of the analyte sensor while the transceiver is in the sleep mode.

18. The analyte sensor system of claim 15, wherein the processor is further configured to:
- cause the transceiver to transmit a third series of advertisement signals after exiting the sleep mode,
- receive a third data connection request from the second display device,
- cause the transceiver to establish a third data connection with the second display device if it is determined that the second display device is identified in the first list,
- cause the transceiver to transmit a third signal to the second display indicating that a different display device is identified in the second list,
- receive a fourth signal from the second display device, the fourth signal indicating that the third display device is not a newly selected active display device, and
- cause the transceiver to terminate the third data connection with the second display device without changing the second list.

\* \* \* \* \*

UNITED STATES PATENT AND TRADEMARK OFFICE
CERTIFICATE OF CORRECTION

PATENT NO. : 9,974,469 B2
APPLICATION NO. : 14/533943
DATED : May 22, 2018
INVENTOR(S) : Jose Hector Hernandez-Rosas et al.

Page 1 of 1

It is certified that error appears in the above-identified patent and that said Letters Patent is hereby corrected as shown below:

In the Drawings

On Sheet 4 of 13 (FIG. 4) at Line 16 (Approx.), Change "Deactive" to --Deactivate--.

In the Specification

In Column 13 at Line 11, Change "andrenostenedione;" to --androstenedione;--.

In Column 13 at Line 27, Change "diptheria/" to --diphtheria/--.

In Column 13 at Line 34, Change "perioxidase;" to --peroxidase;--.

In Column 13 at Line 43, Change "sissomicin;" to --sisomicin;--.

In Column 13 at Line 47, Change "duodenalisa," to --duodenalis,--.

In Column 13 at Line 55, Change "Trepenoma pallidium," to --Treponema pallidum,--.

In Column 13 at Line 56, Change "stomatis" to --stomatitis--.

In Column 14 at Line 9-10, Change "(barbituates," to --(barbiturates,--.

In Column 19 at Line 41, Change "132,/or" to --132, or--.

Signed and Sealed this
Twenty-first Day of August, 2018

Andrei Iancu
*Director of the United States Patent and Trademark Office*